(12) United States Patent
Nemirovsky et al.

(10) Patent No.: US 11,609,217 B2
(45) Date of Patent: Mar. 21, 2023

(54) GAS SENSING DEVICE HAVING DISTRIBUTED GAS SENSING ELEMENTS AND A METHOD FOR SENSING GAS

(71) Applicants: TODOS TECHNOLOGIES LTD., Airport (IL); Technion Research and Development Foundation Ltd., Haifa (IL)

(72) Inventors: Yael Nemirovsky, Haifa (IL); Amikam Nemirovsky, Haifa (IL); Shmuel Melman, Haifa (IL)

(73) Assignees: Todos Technologies Ltd., Airport (IL); TECHNION RESEARCH AND DEVELOPMENT FOUNDATION LTD., Haifa (IL)

( * ) Notice: Subject to any disclaimer, the term of this patent is extended or adjusted under 35 U.S.C. 154(b) by 131 days.

(21) Appl. No.: 16/948,170

(22) Filed: Sep. 4, 2020

(65) Prior Publication Data
US 2020/0400633 A1    Dec. 24, 2020

Related U.S. Application Data

(63) Continuation of application No. 15/748,723, filed as application No. PCT/IL2016/050839 on Aug. 1, 2016, now Pat. No. 10,768,153.

(60) Provisional application No. 62/200,044, filed on Aug. 2, 2015.

(51) Int. Cl.
*G01N 33/00*    (2006.01)
*G01N 25/30*    (2006.01)

(52) U.S. Cl.
CPC ......... *G01N 33/0031* (2013.01); *G01N 25/30* (2013.01); *G01N 33/0027* (2013.01)

(58) Field of Classification Search
CPC .. G01N 27/123; G01N 27/002; G01N 25/005; G01N 9/04; G01N 27/403; G01N 27/304; G01N 27/414; G01N 27/127; G01N 21/59; G01N 27/128; G01N 33/006; G01N 27/22; G01N 27/16; G01N 33/0047; G01N 33/0031; G01N 25/30; G01N 33/0027; C23C 16/52; G01J 5/12; G01F 1/68; G01K 7/30; H05B 3/00; G01P 5/12
See application file for complete search history.

(56) References Cited

U.S. PATENT DOCUMENTS

| | | | |
|---|---|---|---|
| 5,989,398 A * | 11/1999 | Young | G01N 25/30 204/427 |
| 2006/0133960 A1 | 6/2006 | Ahmad | |
| 2009/0126460 A1 * | 5/2009 | Gardner | G01N 33/0047 257/253 |
| 2017/0205366 A1 * | 7/2017 | Nemirovsky | G01N 25/30 |

* cited by examiner

Primary Examiner — Brandi N Hopkins
(74) Attorney, Agent, or Firm — Reches Patents

(57) ABSTRACT

A method for sensing gas by a gas sensing device, the method may include generating, by a semiconductor temperature sensing element that is spaced apart from a gas reactive element and is thermally coupled to the gas reactive element, detection signals that are indicative of a temperature of the gas reactive element; wherein the gas reactive element and the semiconductor temperature sensing element are of microscopic scale; and processing, by a readout circuit of the gas sensing device, the detection signals to provide information about a gas that affected the temperature of the gas reactive element.

15 Claims, 27 Drawing Sheets

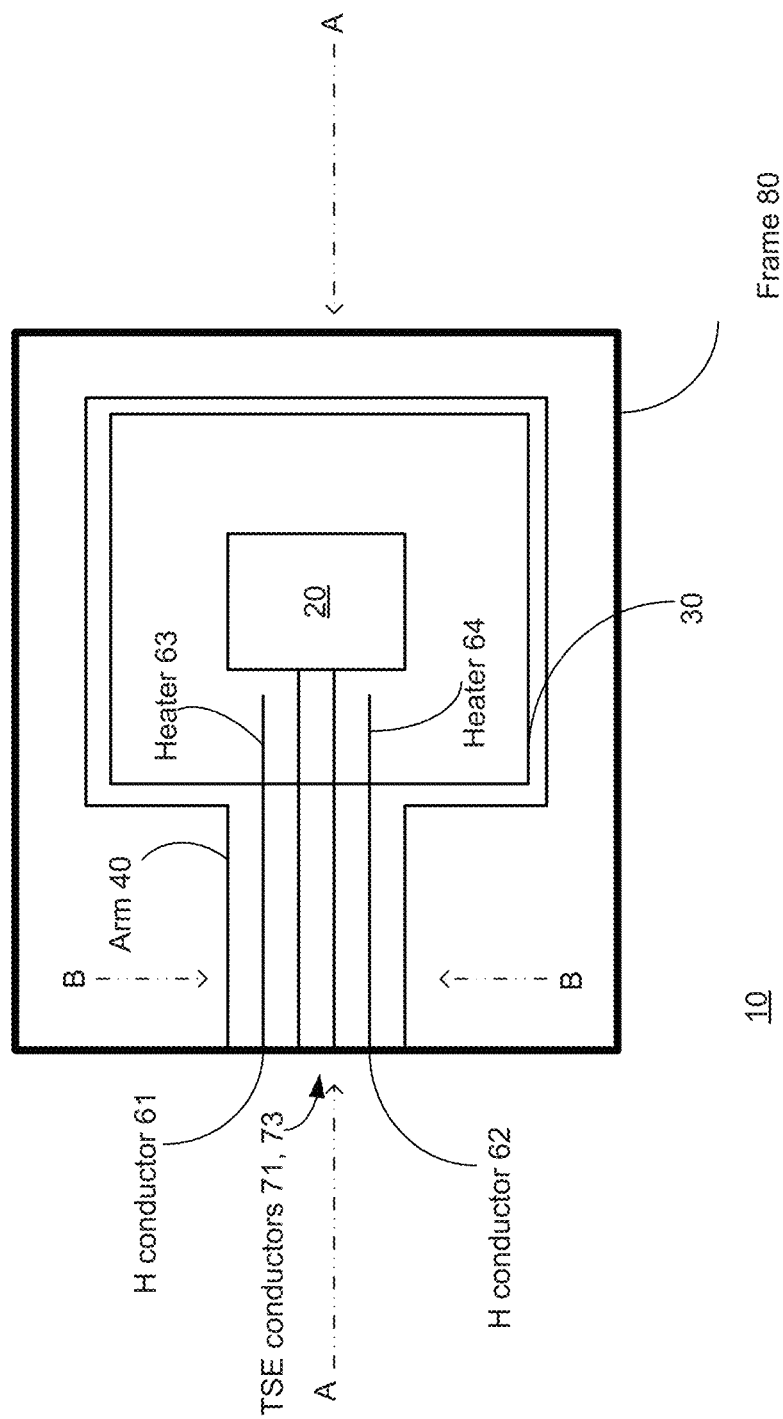

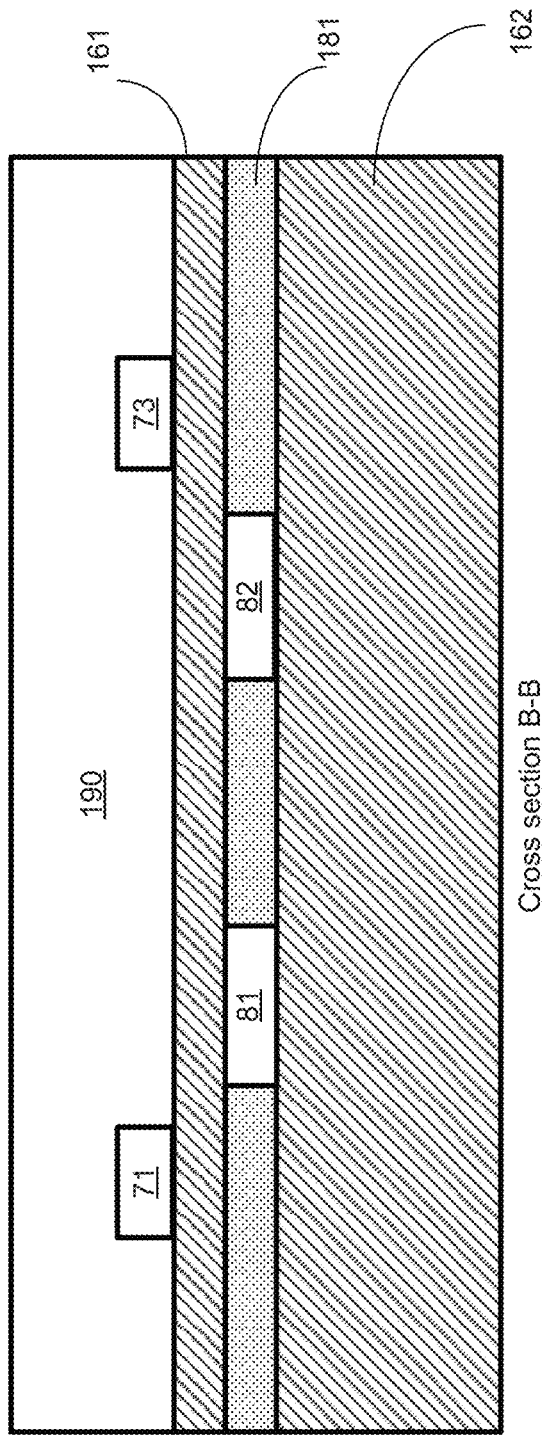
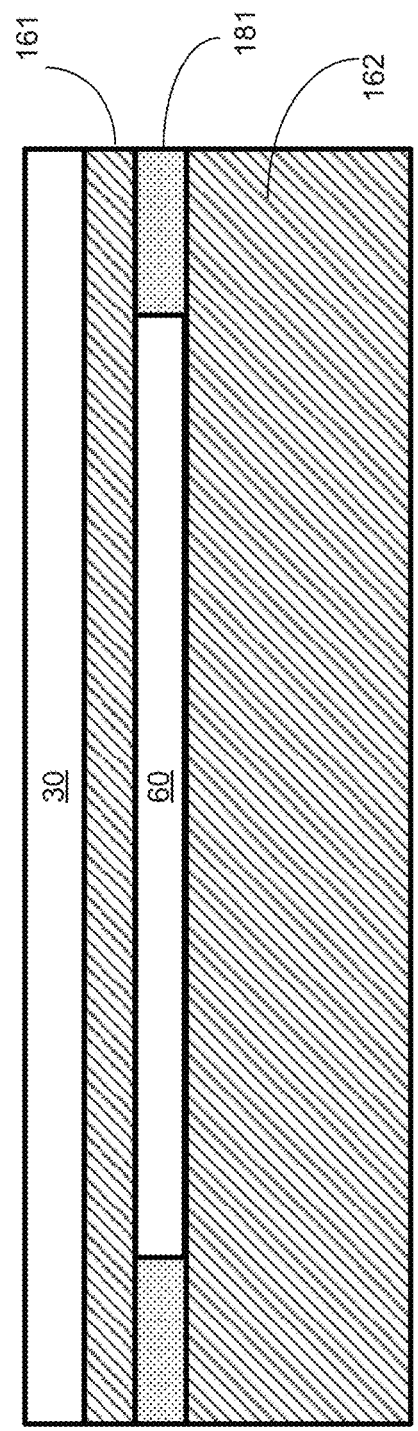

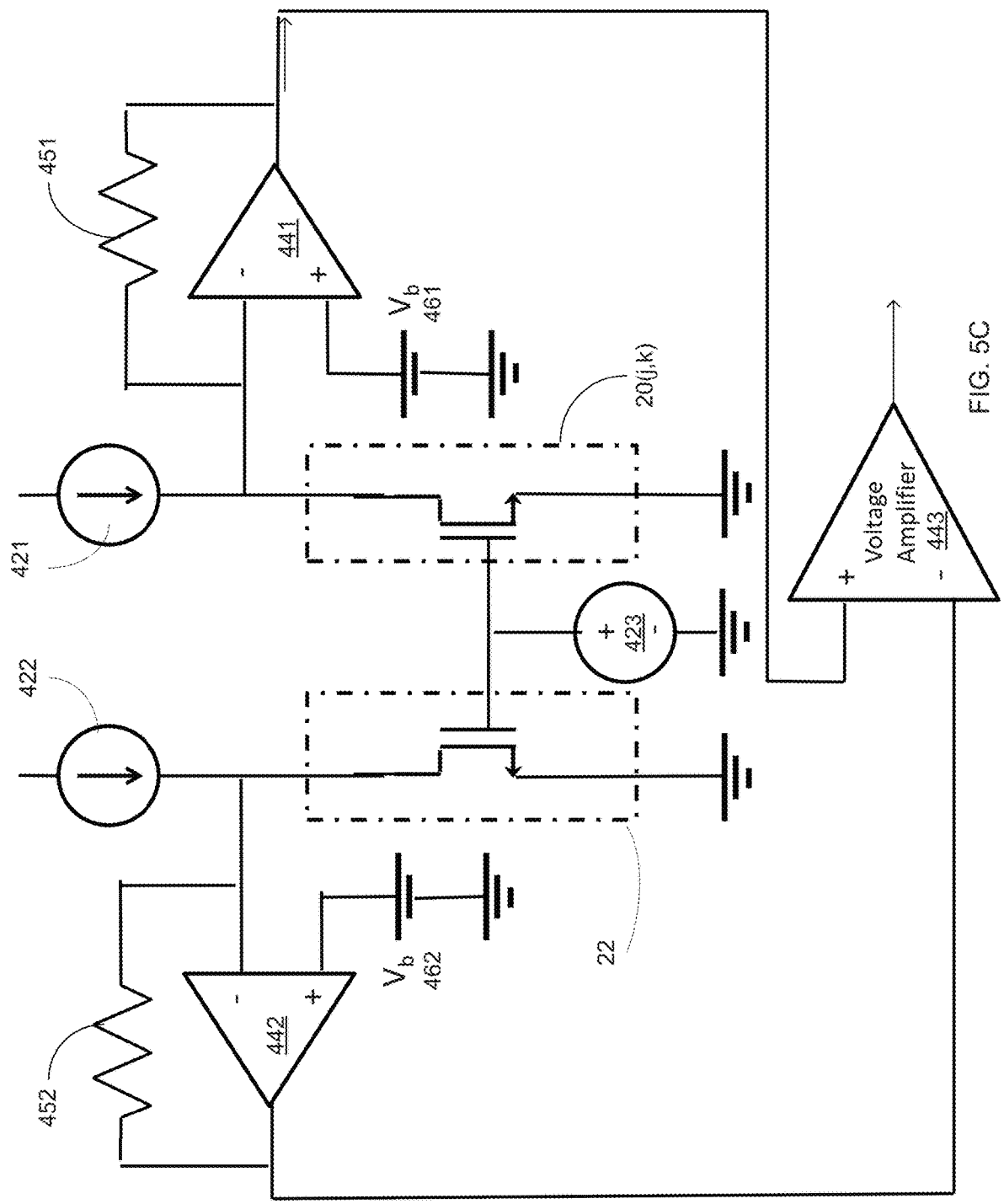

```
┌─────────────────────────────────────────────────────────────────────┐
│ Generating, by a semiconductor temperature sensing element that is  │
│ spaced apart from a gas reactive element and is thermally coupled   │
│ to the gas reactive element, detection signals that are indicative  │
│ of a temperature of the gas reactive element; wherein the gas       │
│ reactive element and the semiconductor temperature sensing element  │
│ are of microscopic scale. 952                                       │
└─────────────────────────────────────────────────────────────────────┘
                                    ↓
┌─────────────────────────────────────────────────────────────────────┐
│ Processing the detection signals to provide information about a gas │
│ that affected the temperature of the gas reactive element. 954      │
└─────────────────────────────────────────────────────────────────────┘

┌─────────────────────────────────────────────────────────────────────┐
│                  Heating the heating element. 951                   │
└─────────────────────────────────────────────────────────────────────┘

┌─────────────────────────────────────────────────────────────────────┐
│ Maintaining vacuum within an enclosure that surrounds the           │
│ semiconductor temperature sensing element. 953                      │
└─────────────────────────────────────────────────────────────────────┘

┌─────────────────────────────────────────────────────────────────────┐
│ Using differential sensing that involve reading detection signals   │
│ from a reference semiconductor temperature sensing element that     │
│ does not sense radiation from a gas reactive element. 955           │
└─────────────────────────────────────────────────────────────────────┘

┌─────────────────────────────────────────────────────────────────────┐
│              Using multiple gas sensing elements. 957               │
└─────────────────────────────────────────────────────────────────────┘
```

GAS SENSING DEVICE HAVING DISTRIBUTED GAS SENSING ELEMENTS AND A METHOD FOR SENSING GAS

CROSS REFERENCE TO RELATED APPLICATIONS

This application is a continuation of U.S. patent application Ser. No. 15/748,723 filing date Jan. 30, 2018 which is a national phase application of PCT patent application PCT/IL2016/050839 filing date Aug. 1, 2016 that claims priority from US provisional patent filing date Aug. 2, 2015, Ser. No. 62/000,044—all of which is incorporated herein by reference.

BACKGROUND OF THE INVENTION

Resistance-based gas sensing devices are inaccurate. The resistance of the gas sensing device can vary according to various parameters that are not related to the gas that is detected. For example—an adsorption of oxygen/oxidizing gases increases resistance of an n-type gas sensing device while an adsorption (on surface) of the gas that is being detected (reducing gases) decreases the resistance. Furthermore—the gas flow may affect the resistance of the gas sensing element.

There is a growing need to provide a reliable gas sensing device.

SUMMARY

According to an embodiment of the invention there may be provided a gas sensing device that may include a (a) gas reactive element that has a gas dependent temperature parameter; and (b) a semiconductor temperature sensing element that may be spaced apart from the gas reactive element and may be configured to sense radiation emitted from the gas reactive element and generate detection signals that may be responsive to a temperature of the gas reactive element; the gas reactive element and the semiconductor temperature sensing element may be of microscopic scale.

The gas sensing device may include a heating element that may be thermally coupled to the gas reactive element and may be configured to supply a predefined amount of heat to the gas reactive element.

The gas sensing device may include a heating element that may be thermally coupled to the gas reactive element and may be configured to heat the gas reactive element to a predefined temperature.

The heating element and the gas reactive element may be thermally coupled to each other through a thermally conductive and electrical isolating element.

The gas sensing device may include an enclosure; the semiconductor temperature sensing element may be located within the enclosure and the gas reactive element may be not located within the enclosure.

The enclosure may be configured to maintain a vacuum.

The gas reactive element may be connected to the enclosure.

The gas reactive element may be not connected to the enclosure.

The may include a reference semiconductor temperature sensing element that may be not thermally coupled to a gas reactive element and may be configured to detect heat generated by a reference heating element.

The gas sensing device may include gas reactive elements and semiconductor temperature sensing elements, the gas reactive elements and the semiconductor temperature sensing elements may be spaced apart from each other; each gas reactive element of the gas reactive elements has a gas dependent temperature parameter; and each semiconductor temperature sensing elements of the semiconductor temperature sensing elements may be configured to sense radiation emitted from one of the gas reactive elements and generate detection signals that may be responsive to a temperature of the gas reactive element.

The semiconductor temperature sensing element may be thermally isolated from each other.

The gas sensing device may include at least one reference semiconductor temperature sensing element that may be not thermally coupled to any of the gas reactive elements.

At least two gas sensing elements may be configured to sense different gases; each gas sensing element may include a gas reactive element and semiconductor temperature sensing element that may be thermally coupled to the gas reactive element.

At least two gas sensing elements of the array differ from each other by their gas reactive elements; each gas sensing element may include a gas reactive element and semiconductor temperature sensing element that may be thermally coupled to the gas reactive element.

At least two gas sensing elements of the array have a same gas reactive element; each gas sensing element may include a gas reactive element and semiconductor temperature sensing element that may be thermally coupled to the gas reactive element.

At least one gas reactive element may be thermally coupled to a heating element that may be configured to heat the gas reactive element to at least one predefined temperature.

Each heating element may be a polysilicon resistor.

The at least one predefined temperature may include multiple predefined temperatures that may be associated with a sensing of multiple gases that differ from each other; each heating element may be configured to heat the gas reactive element, at different points in time, to different predefined temperatures of the multiple predefined temperatures.

Each heating element may be configured to heat the gas reactive element in a non continuous manner.

The as sensing elements may include N gas sensing elements that may be configured, at a certain point in time, to differ from each other by their response to gases; the gas sensing device may be configured to detect a composition of up till N different gaseous materials by processing the detection signals from semiconductor temperature sensing elements thermally coupled to the N gas sensing elements.

There may be provided a method for sensing gas by a gas sensing device, the method may include generating, by a semiconductor temperature sensing element that may be spaced apart from a gas reactive element and may be thermally coupled to the gas reactive element, detection signals that may be indicative of a temperature of the gas reactive element; the gas reactive element and the semiconductor temperature sensing element may be of microscopic scale; and processing, by a readout circuit of the gas sensing device, the detection signals to provide information about a gas that affected the temperature of the gas reactive element.

The method may include supplying to a heating element that may be thermally coupled to the gas reactive element, a predefined amount of heat to the gas reactive element.

The method may include heating the gas reactive element to a predefined temperature, by a heating element that may be thermally coupled to the gas reactive element.

The heating element and the gas reactive element may be thermally coupled to each other through a thermally conductive and electrically isolating element.

The semiconductor temperature sensing element may be located within the enclosure and the gas reactive element may be not located within the enclosure.

The method may include maintaining vacuum within the enclosure.

The gas reactive element may be connected to the enclosure.

The gas reactive element may be not connected to the enclosure.

The method may include detecting, by a reference semiconductor temperature sensing element, heat generated by a reference heating element; the reference semiconductor temperature sensing element may be not thermally coupled to a gas reactive element.

The method may include generating, by each semiconductor temperature sensing element of semiconductor temperature sensing element, detection signals that may be indicative of a temperature of a gas reactive element out of gas reactive elements; the gas reactive elements and the semiconductor temperature sensing elements may be of microscopic scale; and processing, by the readout circuit of the gas sensing device, the detection signals to provide information about one or more gases that affected the temperatures of the gas reactive elements.

The semiconductor temperature sensing element may be thermally isolated from each other.

The method nay include generating reference detection signals by at least one reference semiconductor temperature sensing element that may be not thermally coupled to any of the gas reactive elements.

The method may include sensing, by at least two gas sensing elements, different gases; each gas sensing element may include a gas reactive element and semiconductor temperature sensing element that may be thermally coupled to the gas reactive element.

At least two gas sensing elements of the array differ from each other by their gas reactive elements; each gas sensing element may include a gas reactive element and semiconductor temperature sensing element that may be thermally coupled to the gas reactive element.

At least two gas sensing elements of the array have a same gas reactive element; each gas sensing element may include a gas reactive element and semiconductor temperature sensing element that may be thermally coupled to the gas reactive element.

The method may include heating at least one gas reactive element, by at least one heating element that may be thermally coupled to the at least one gas reactive element, to at least one predefined temperature.

The heating element may be a polysilicon resistor.

At least one predefined temperature may include multiple predefined temperatures that may be associated with a sensing of multiple gases that differ from each other; the method may include heating, by each heating element of the at least one heating elements, the at least one gas reactive element, at different points in time, to different predefined temperatures of the multiple predefined temperatures.

The method may include heating, by each heating element, a gas reactive element in a non continuous manner.

The gas sensing elements may include N gas sensing elements; the method may include setting the N gas sensing elements, at a certain point in time, to sense different gases; and detecting a composition of up till N different gaseous materials by processing the detection signals from the N gas sensing elements.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 1B illustrates a frame, an arm, a gas sensing element and various conductors according to an embodiment of the invention;

FIG. 2B illustrates a cross section of an arm and various conductors and a cross section of a gas sensing element according to various embodiments of the invention;

FIG. 5C illustrates a gas sensing element, a reference element, current sources, voltage sources, transimpedance amplifiers, a voltage amplifier and feedback resistors according to an embodiment of the invention;

FIG. 20 illustrates a method according to an embodiment of the invention.

Figure 1A:
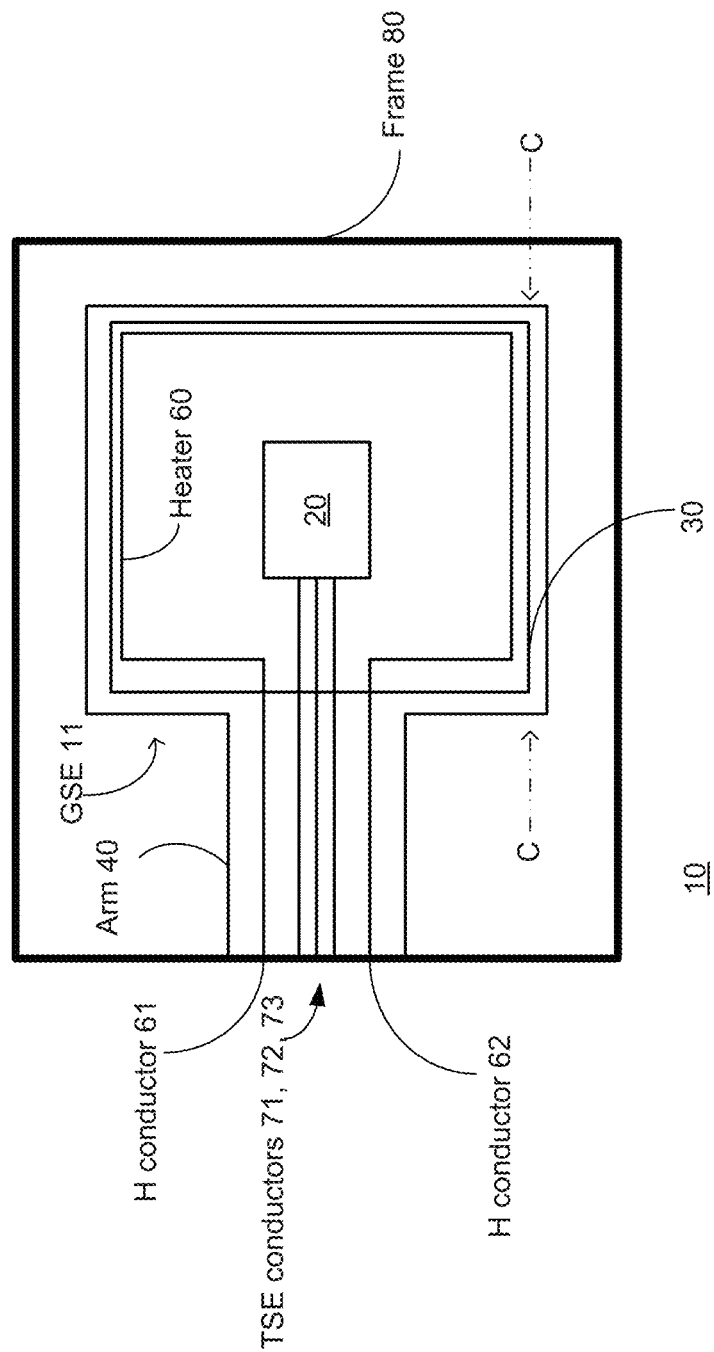
FIG. 1A illustrates a frame, an arm, a gas sensing element and various conductors according to an embodiment of the invention.

It will be appreciated that for simplicity and clarity of illustration, elements shown in the Figures have not necessarily been drawn to scale. For example, the dimensions of some of the elements may be exaggerated relative to other elements for clarity. Further, where considered appropriate, reference numerals may be repeated among the Figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings.

Because the illustrated embodiments of the present invention may for the most part, be implemented using electronic components and circuits known to those skilled in the art, details will not be explained in any greater extent than that considered necessary as illustrated above, for the understanding and appreciation of the underlying concepts of the present invention and in order not to obfuscate or distract from the teachings of the present invention.

Any reference in the specification to a method should be applied mutatis mutandis to a gas sensing device capable of executing the method.

Any reference in the specification to a gas sensing device should be applied mutatis mutandis to a method that may be executed by the gas sensing device.

FIG. 1A illustrates a frame 80, an arm 40, a gas sensing element (GSE) 11 and various conductors according to an embodiment of the invention.

Gas sensing element 11 is illustrates as including (i) a gas reactive element 30 that has a gas dependent temperature parameter; (ii) a semiconductor temperature sensing element 20 that is thermally coupled to the gas reactive element 30 and is configured to generate detection signals that are responsive to a temperature of the gas reactive element 30, and (iii) heater 60.

Heater 60 may be configured to heat the gas reactive element 30 to a predefined temperature that is suited (for that gas reactive element 30) for sensing a predefined gas. Gas reactive elements 30 made of different materials may sense different gases. Additionally or alternatively, heating a gas reactive element to different predefined temperatures will assist in detecting different gases.

The gas reactive element 30 can be made of a catalytic metal. A chemical reaction between the gas reactive element 30 and a certain gas may change the temperature of the gas reactive element 30. The semiconductor temperature sensing element 20 is thermally coupled to the gas reactive element and thus is able to sense the temperature of the gas reactive element 30. It is noted that the heating device may be omitted from the gas sensing element.

Gas sensing element 11 may be suspended—it is positioned above a bulk (not shown) and is thermally isolated from the bulk.

Arm 40 supports the gas sensing element 11 as well as supports conductors such as heater conductors 61 and 62 and semiconductor temperature sensing element (TSE) conductors 71, 72 and 73. Arm 40 is connected to or interfaces with frame 80.

The TSE conductors should be electrically conductive but have a poor thermal conduction (at least have a thermal conduction below a predefined threshold) in order to reduce and even eliminate any thermal effect that the bulk may have on the semiconductor temperature sensing element 20. The TSE conductors can be made, for example, from doped polysilicon or active silicon.

The semiconductor temperature sensing element 20 may be a transistor such as a CMOS transistor and TSE conductors 71, 72 and 73 may be electrically coupled to a source, a drain and a gate of the CMOS transistor.

It is noted that the CMOS transistor may have its gate and drain shorted and may be fed by a pair of TSE conductors.

It is noted that the semiconductor temperature sensing element 20 may differ from a CMOS transistor.

Heater 60 may be fed by heater conductors 61 and 61. Heater 60 may be fed with continuous or non-continuous signals for activating the heater 60. For example, heater 60 may be provided (via heater conductors 61 ad 62) with current pulses that may heat the heater 60 to a predefined temperature.

In FIG. 1A heater 60 surrounds semiconductor temperature sensing element 20.

The heater conductors 61 and 62 may be made of Doped polysilicon, active silicon, aluminum or any other metal.

In FIG. 1A the heater 60 is positioned above the semiconductor temperature sensing element 20. It is noted that heater 60 may be positioned at the same height as the semiconductor temperature sensing element 20—and is preferably spaced apart from the semiconductor temperature sensing element 20.

FIG. 1A illustrates an imaginary plane C-C. FIG. 2B illustrates a cross section along plane C-C.

FIG. 1B illustrates frame 80, an arm 40, a gas sensing element (GSE) 11 and various conductors according to another embodiment of the invention.

In FIG. 1B there are only two TSE conductors 71 and 73 and the semiconductor temperature sensing element 20 is not surrounded by a heater—as illustrated by heater portions 63 and 64.

In FIG. 1B the semiconductor temperature sensing element 20 can be a CMOS diode or any other diode as well as a transistor that is coupled as a diode.

Figure 2A:
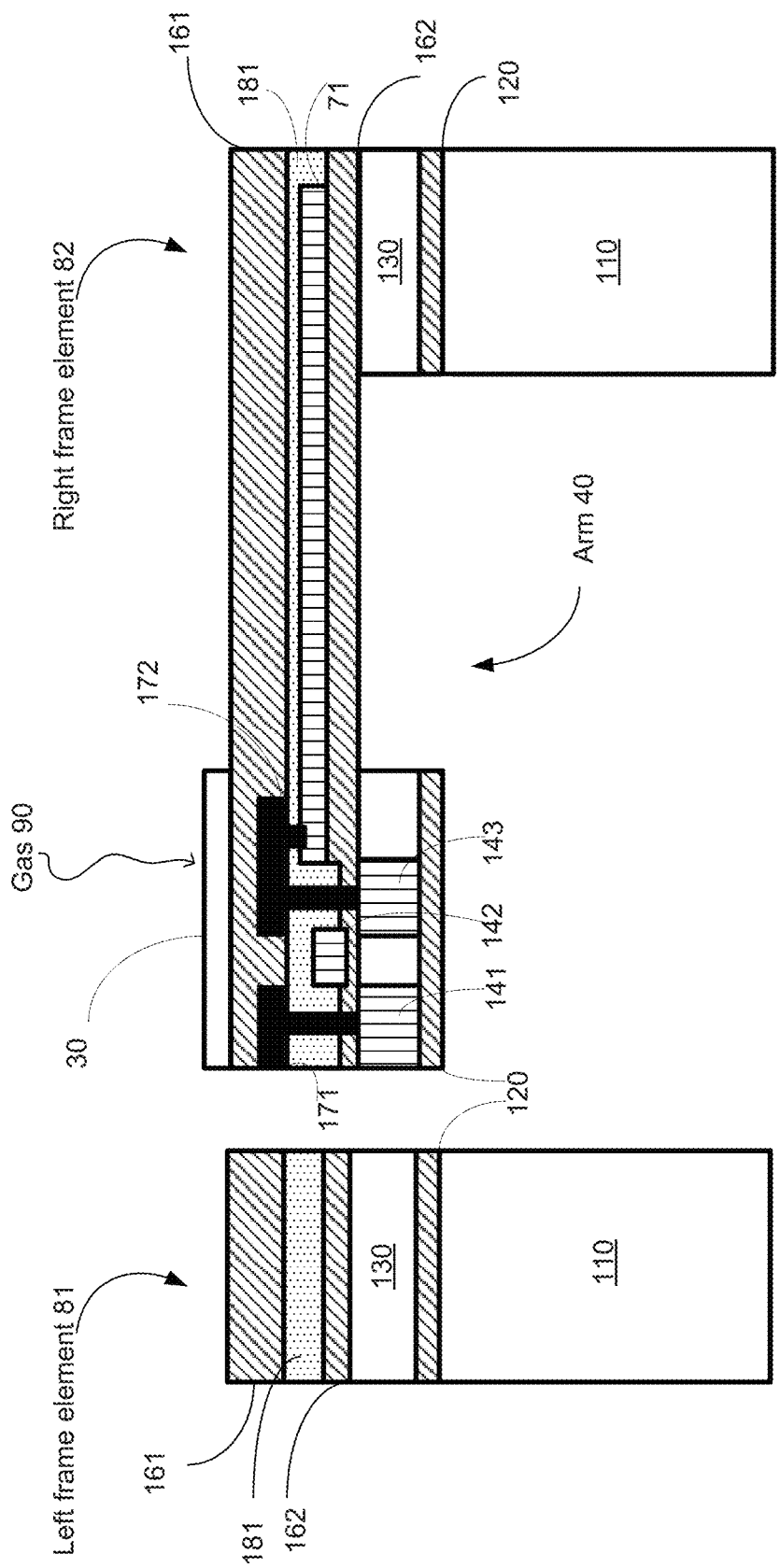
FIG. 2A is a cross sectional view of a frame, an arm and a gas sensing element according an embodiment of the invention.

FIG. 1B illustrates imaginary planes A-A and B-B. FIG. 2A illustrates a cross section along plane A-A. FIG. 2B illustrates a cross section along plane B-B.

Figure 1C:
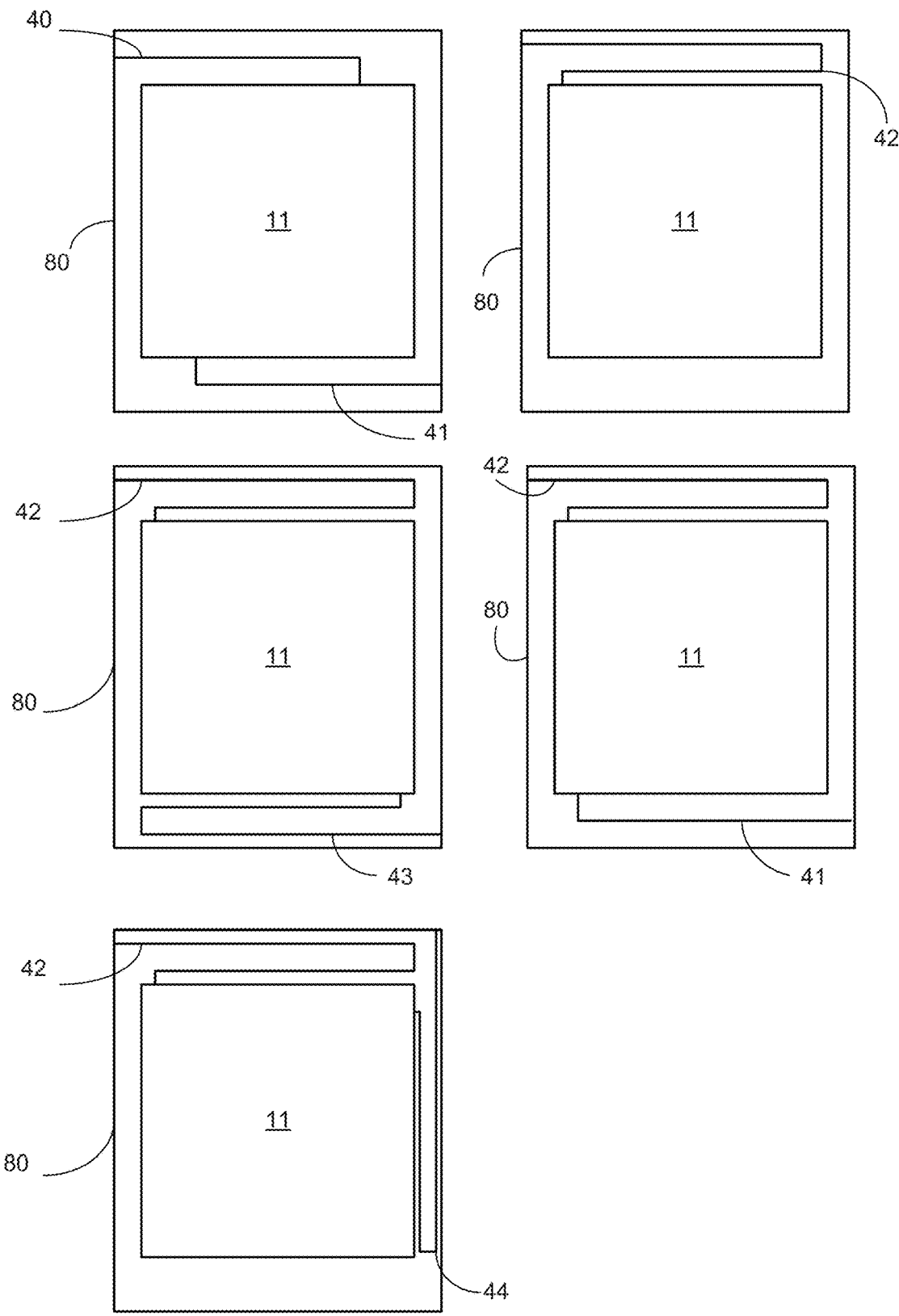
FIG. 1C illustrates a frame, various arms, and various gas sensing elements according to various embodiments of the invention.

FIG. 1C illustrates a frame 80, various arms 40, 41, 42, 43 and 44 and various gas sensing elements 11 according to various embodiments of the invention.

FIG. 1C illustrates that a gas sensing element 11 may be supported by one arm or more arms (for example two arms), and that the arms may have different shapes.

The shape and size of the arms may change. As a rule of thumb longer arms (for example arms 42, 43 and 44) provide better thermal isolation from shorter arms (for example arms 40 and 41) that are made of the same materials.

FIG. 2A is a cross sectional view (along plane A-A) of a frame, an arm and a gas sensing element according an embodiment of the invention.

Frame 80 is illustrated as has having a left frame element 81 and a right frame element 82.

FIG. 2A illustrates a semiconductor temperature sensing element such as a CMOS transistor that includes drain 141, source 143 and gate 142. Drain 141 is coupled to a drain conductor 171. Source 143 is coupled to a source conductor 172. Source conductor 171 and drain conductor 172 are made of metal and may be coupled to TSE conductors 71 and 72 respectively. The gate 142 may be coupled to a gate conductor (now shown).

Drain 141 and source 143 may be positioned above a thin silicon dioxide layer 120 that can be formed on top of thick silicon bulk 110.

Bulk 110 and device layer 130 may be micro-machined or nano-machined to form a suspended gas sensing element.

Thin silicon dioxide layer 120 of the buried oxide may serve as an etch stop layer for the bulk micromachining process and separates the bulk silicon from the thin device single crystal silicon layer 130.

The stack of thin device silicon layer 130 on top of thin silicon dioxide layer 120 on top of thick silicon bulk 110 is known as SOI and may be fabricated by several techniques, well known for the experts. An increase in the top silicon layer thickness, and increased control of its properties, is preferably achieved using epitaxial growth of silicon.

The non-etched silicon bulk 110 serves as a heat sink to the thermal sensors due to the high thermal conductivity of the silicon and the large thickness of silicon bulk 110. Silicon bulk 110 is etched under the sensor area in order to provide thermal isolation for increased temperature responsivity.

Above the etched area a structure composed of layers such as but not limited to Complementary Metal Oxide Semiconductor (CMOS) thin film layers—such as first insulating layers 161 and second insulating layer 162—both known as Inter Level Dielectrics.

FIG. 2A illustrate a TSE conductor 171 that is coupled to source conductor 172. First and second insulating layers 161 and 162 and separated by intermediate layer 181.

Non-limiting dimensions of are provided below:

| Element | Dimensions (in Angstrom) |
| --- | --- |
| Gas reactive element 30 | 100-500 (Thickness) |
| First insulating layer 161 | 4000 (Thickness) |
| Source conductor 171 (horizontal part) | 330-2600 (Thickness) |
| Buried oxide 120 | 4000-10000 (Thickness) |
| Gate oxide 142 | 20-50 (Thickness), |
| Source 141 and drain 143 | 145-150 (Thickness) |
| Polysilicon Gate | 2000 A |

FIG. 2B illustrates a cross section of an arm and various conductors and a cross section of a gas sensing element according to various embodiments of the invention.

FIG. 2B illustrates a cross section of arm 40 taken along plane B-B.

Arm 40 includes heater conductors 61 and 62 as well as TSE conductors 72 and 73. Heater conductors 81 and 82 are formed in intermediate layer 181. TSE conductors 72 and 73 are form in a top layer 190. First insulating layer 161 is positioned between top layer 190 and intermediate layer 181. Intermediate layer 181 is supported by second insulating layer 162.

FIG. 2B also illustrates a cross section of the gas sensing element along plane C-C. This cross section includes the gas reactive element 30 on top of layer 161, on top of heater 60 and surrounding elements and on top of layer 162.

Heater 60 is formed in intermediate layer 181. Gas reactive element 30 is positioned above first insulating layer 161.

First insulating layer 161 can be made of a dielectric layer composed of oxide or nitride.

Figure 3A:
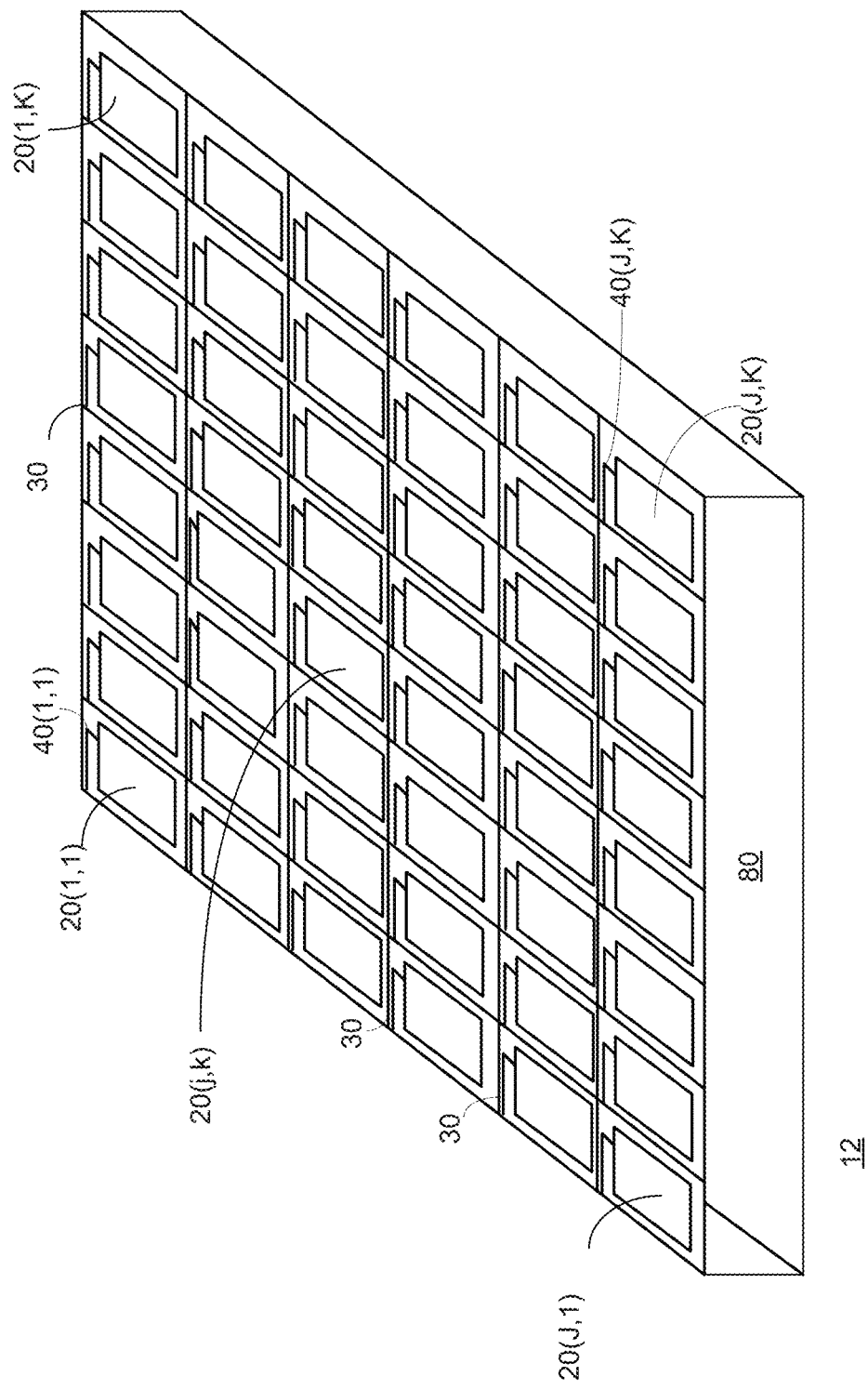
FIG. 3A illustrates frame, arms and an array of gas sensing elements according to an embodiment of the invention.

FIG. 3A illustrates an array of gas sensing elements, according to various embodiments of the invention.

FIG. 3A illustrates a rectangular array of gas sensing elements 20(1,1)-20(J,K) that include K columns and J rows of gas sensing elements. J and K are positive integers that exceed one.

Different gas sensing elements of the array may be configured to sense the same gas or different gases. A composition of the gas reactive element and, additionally or alternatively, a temperature to which the gas reactive element is heated may determine which gas is sensed by the gas reactive element.

The gas sensing elements of the array are supported by arms 40(1,1)-40(J,K) to a grid of frames collectively denoted 80.

Each gas sensing element may be connected to one or more arms.

Figure 3B:
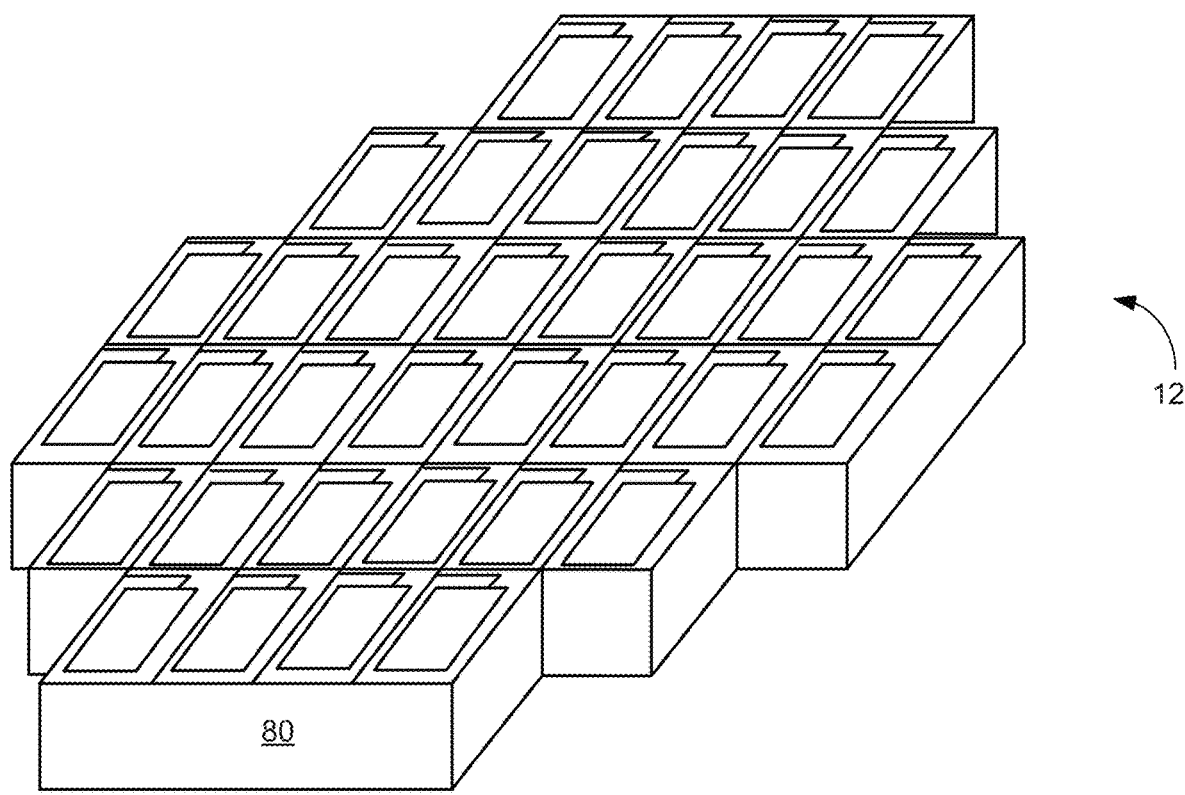
FIG. 3B illustrates frames, arms and an array of gas sensing elements according to an embodiment of the invention.

The gas sensing elements may be arranged to form other arrays. For example—a linear array, a non-rectangular array, a polygonal array, a circular array or any arrangements of multiple sensing elements. FIG. 3B illustrates a non-rectangular array of gas sensing elements.

The gas sensing elements in the array may be connected electrically in parallel or serially or in a combination of serially and parallel configurations in order to maximize the signal to noise.

Gas sensing elements that are configured to sense different materials may be used for sensing gaseous mixtures that include different materials. For example if there are N gas sensing elements and each gas sensing element is configured to sense a different material (or otherwise has a different response to materials that the other gas sensing elements) than the N gas sensing element may detect a composition of up till N different gaseous materials.

For example, assuming four different gas sensing elements and a gaseous mixture of four different materials:

$$\begin{bmatrix} A11 & A12 & A13 & A14 \\ A21 & A22 & A23 & A24 \\ A31 & A32 & A33 & A34 \\ A41 & A42 & A43 & A44 \end{bmatrix} * \begin{bmatrix} G1 \\ G2 \\ G3 \\ G4 \end{bmatrix} = \begin{bmatrix} O1 \\ O2 \\ O3 \\ O4 \end{bmatrix} \quad (1)$$

$$\begin{bmatrix} A11 & A12 & A13 & A14 \\ A21 & A22 & A23 & A24 \\ A31 & A32 & A33 & A34 \\ A41 & A42 & A43 & A44 \end{bmatrix}^{-1} * \begin{bmatrix} O1 \\ O2 \\ O3 \\ O4 \end{bmatrix} = \begin{bmatrix} G1 \\ G2 \\ G3 \\ G4 \end{bmatrix} \quad (2)$$

Equation (1) illustrates that the detection signals of each gas sensing element are a superposition of the reactions of the gas sensing element to each one of the components of the gaseous mixture. Equation (2) is extracted from equation (1).

G1, G2, G3 and G4 are the concentrations of the first, second, third and fourth materials of the gaseous mixture. O1, O2, O3 and O4 are the detection signals of the first, second, third and fourth gas sensing elements and for indexes i and j that range between 1 and 4 Aij is the reaction coefficient of the i'th gas sensing element to the j'th material of the gaseous mixture.

Figure 4A:
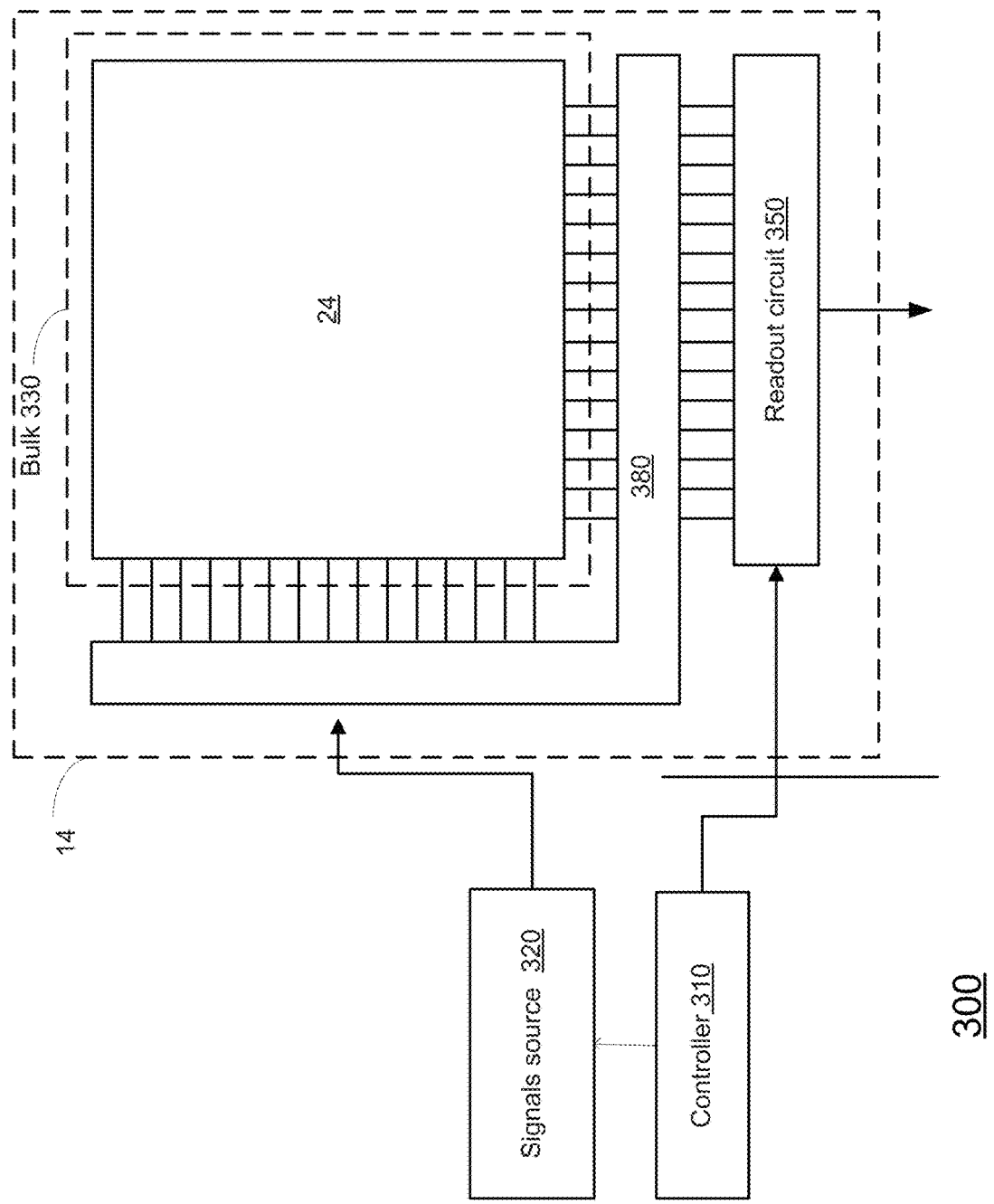
FIG. 4A illustrates a gas sensing device according to an embodiment of the invention.

FIG. 4A illustrates a gas sensing device 300 according to an embodiment of the invention.

Gas sensing device 300 includes a controller 310, signals source 320, bulk 330, interfacing module 380, readout circuit 350 and an array 24 of gas sensing elements.

Although interfacing module 380 is illustrates as a separate entity from the array 24, both array 24 and interfacing module 380 may be integrated.

Interfacing module 380 may couple between the array 24 to the signals source 320 and to the readout circuit 350.

Readout circuit 350 may read detection signals from one or more gas sensing elements at a time. For example—the readout circuit 350 may read a single row of array 24, a part of a row, more than a single row, a column, a part of a column, more than a column and even the entire array at once.

Readout circuit 350 may read current detection signals, voltage detection signals, differential detection signals and the like.

Gas sensing device 300 may include reference sensing elements. The reference sensing elements may be included in array 24 or outside array 24. A reference sensing element has a semiconductor temperature sensing element but does not include a gas reactive element. Alternatively, the semiconductor temperature sensing element is not thermally coupled to the gas relative element or otherwise is not substantially affected by gas reactions.

According to an embodiment of the invention the interfacing module 380 may also electrically couple between different gas sensing elements of the array 24. The interfacing module 380 may couple certain gas sensing elements of the array in serial to each other during one measurement and couple the certain gas sensing elements of the array in parallel to each other during another measurement. Any combination of serial and parallel couplings between gas sensing elements may be provided. The interfacing module 380 may include any combination of switches, interconnects and the like.

Signals source 310 is configured to supply bias signals to at least one gas sensing element of the array 24. The bias signals may include voltage bias signals and/or current bias signals. Some bias signals may set one or more semiconductor temperature sensing elements to one or more desired working points. Other bias signals may determine the heating applied by one or more heaters.

The bias signals may be provided in a continuous manner or in a non-continuous manner. The latter may reduce the power consumption of the gas sensing device. Conveniently, a first pulse aimed to bias a semiconductor temperature sensing elements of a certain gas sensing element is synchronized with a second pulse aimed to bias a heater of the certain gas sensing element. The second pulse may begin before the first pulse. The first and second pulse may be partially overlapping, fully overlapping or non-overlapping.

Controller 310 is configured to control the operation of the gas sensing device 300.

Controller 310, signals source 320, bulk 330, interfacing module 380, readout circuit 350 and array 24 of gas sensing elements may be formed on the same chip. The gas sensing device 300 may be fabricated using CMOS technology.

Figure 4B:
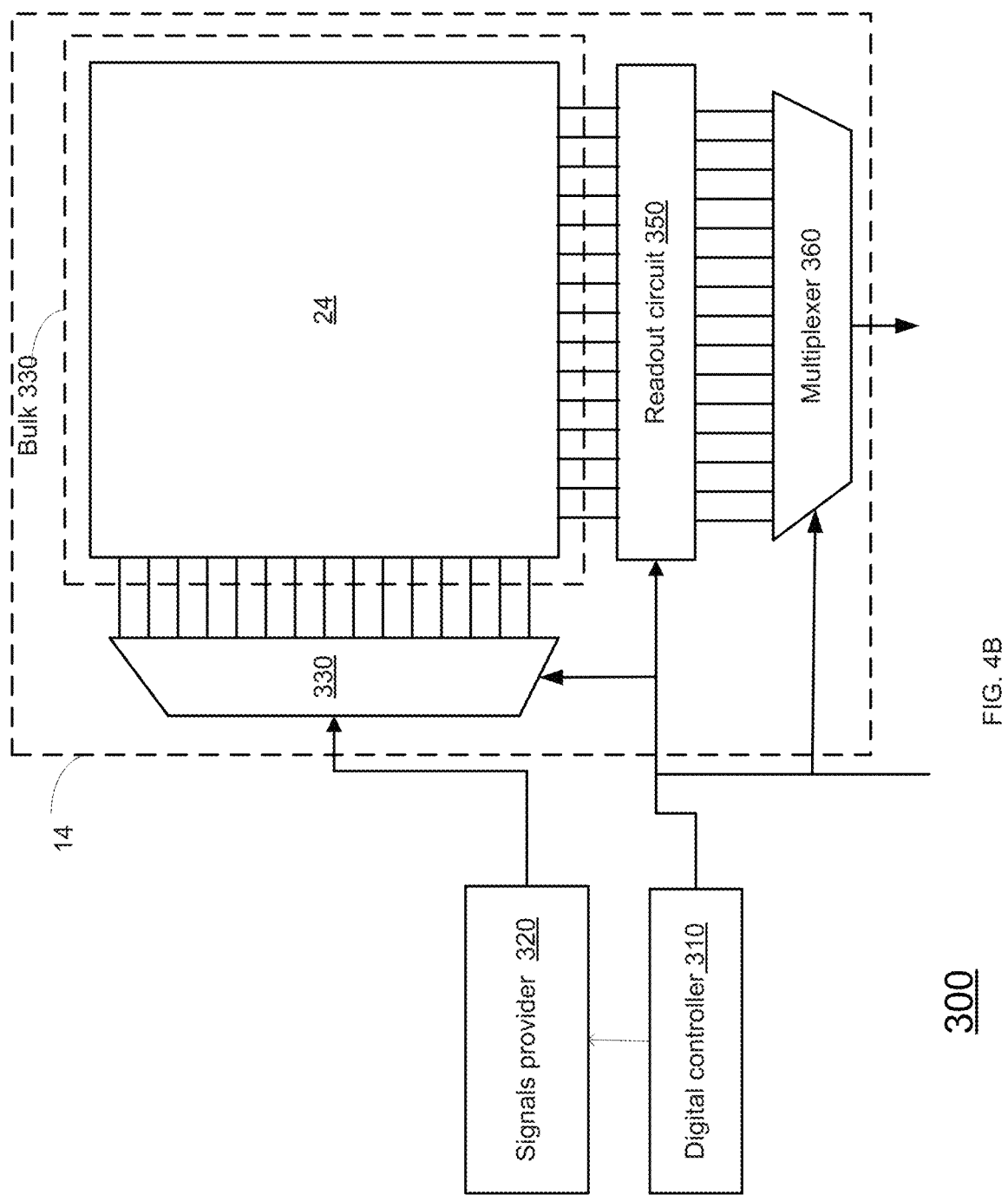
FIG. 4B illustrates a gas sensing device according to an embodiment of the invention.

FIG. 4B illustrates a gas sensing device 300 according to an embodiment of the invention.

In FIG. 4B the interfacing module 380 is illustrates as including (i) a demultiplexer 330 that is coupled between signals source (also referred to as signals provider) 320 and array 24, and (ii) a multiplexer 360 that is coupled between readout circuit 350 and an output port of gas sensing device.

Figure 5A:
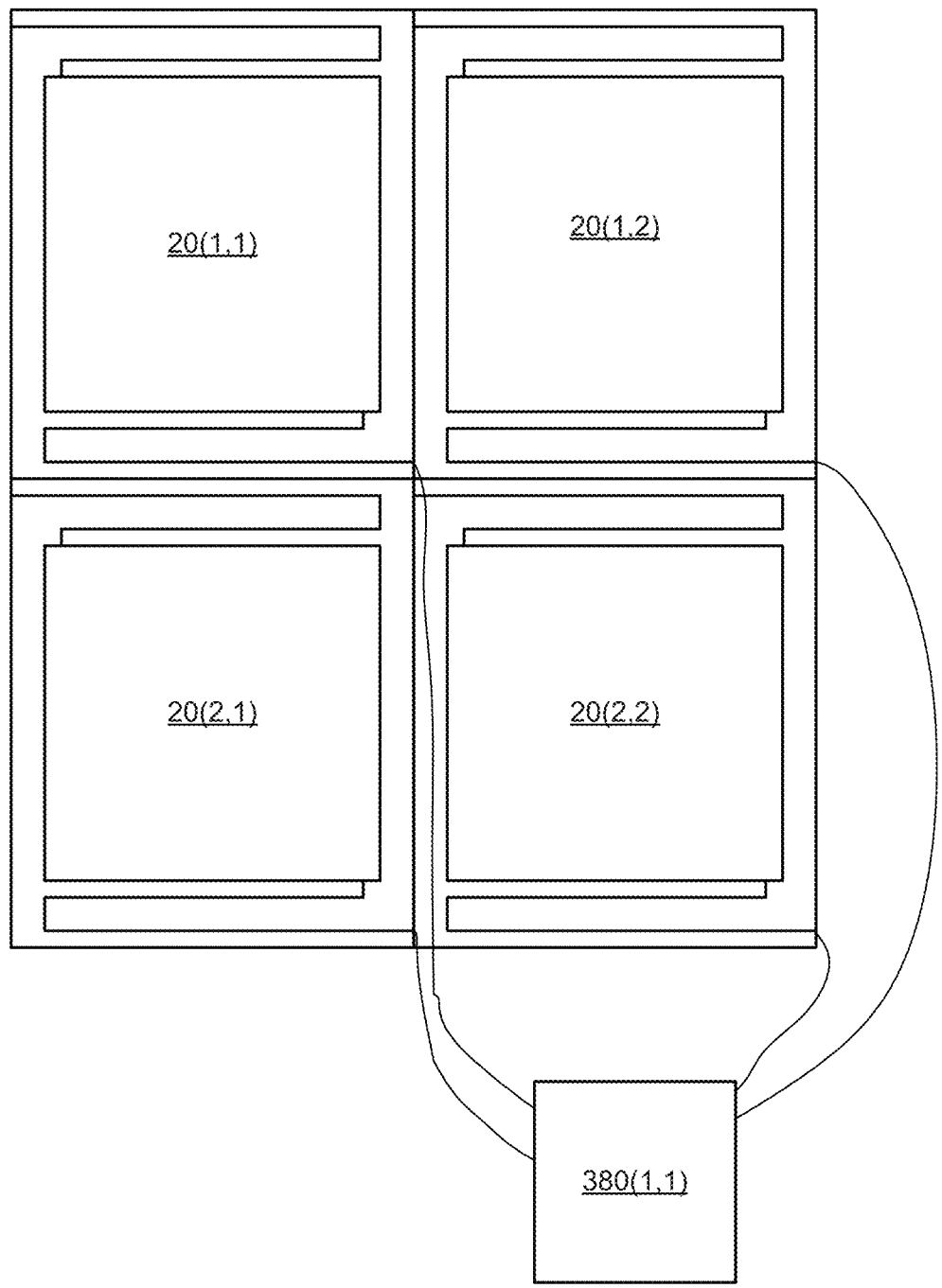
FIG. 5A illustrates gas sensing elements and a part of an interfacing module according to an embodiment of the invention.

FIG. 5A illustrates gas sensing elements 20(1,1), 20(1,2), 20(2,1) and 20(2,2) and a part 380(1,1) of an interfacing module according to an embodiment of the invention.

Part 380(1,1) may provide bias signals to each one of gas sensing elements 20(1,1), 20(1,2), 20(2,1) and 20(2,2) and may receive and/or manipulate detection signals from gas sensing elements 20(1,1), 20(1,2), 20(2,1) and 20(2,2).

For example, part 380(1,1) may perform a manipulation by adding (or averaging) the detection signals from gas sensing elements 20(1,1), 20(1,2), 20(2,1) and 20(2,2).

When each one of gas sensing elements gas sensing elements 20(1,1), 20(1,2), 20(2,1) and 20(2,2) is used to sense different materials then gas sensing elements 20(1,1), 20(1,2), 20(2,1) and 20(2,2) are capable of detecting a gaseous mixture of up till four different materials.

Each gas sensing element may have a different response to materials—and when exposed to a gaseous mixture of up till four different materials the processing of detection signals of gas sensing elements 20(1,1), 20(1,2), 20(2,1) and 20(2,2) can reveal the composition of the gaseous mixture.

Figure 5B:
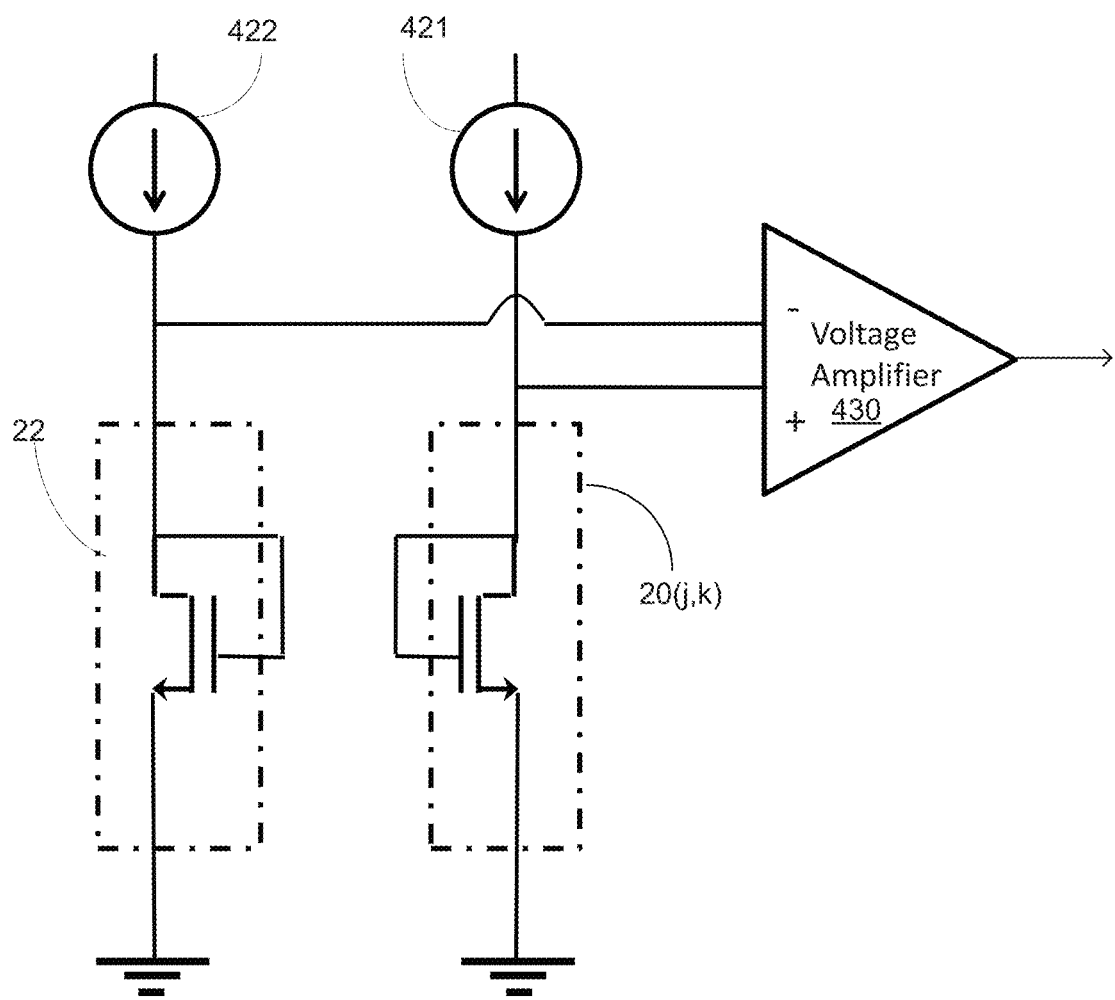
FIG. 5B illustrates a gas sensing element, a reference element, current sources and a voltage amplifier according to an embodiment of the invention.

FIG. 5B illustrates a gas sensing element 20(j,k), a reference element 22, current sources 421 and 422 and a voltage amplifier 430 according to an embodiment of the invention.

Each one of gas sensing element 20(j,k) and reference element 22 has a CMOS transistor that is coupled as a diode but may also be operated with 3 terminals. A detection signal is outputted by gas sensing element 20(j,k) and is a voltage detection signal. The detection signal reflects the gas sensed by the gas sensing element—especially the temperature of the gas reactive element of gas sensing element 20(j,k). A reference signal is a voltage detection signal and reflects the temperature of the CMOS transistor of reference element 22.

The detection signal is fed to a non-inverting input of voltage amplifier 430. The reference signal is fed to an inverting input of voltage amplifier 430. Voltage amplifier 430 calculates the difference between the detection signal and the reference signal.

The reference signal may be provided by any reference source—including a voltage source that does not include a CMOS transistor.

Current sources 421 and 422 may belong to signals source 320 and are provided, via interfacing module 380, to gas sensing element 20(j,k) and reference 22 respectively.

Voltage amplifier 430 may belong to readout circuit 350 of FIGS. 4A and 4B. Voltage amplifier 350 may receive the detection signal via interfacing module 380.

FIG. 5C illustrates a gas sensing element 20(j,k), a reference element 22, current sources 421 and 422, voltage sources 423, 461 and 462, transimpedance amplifiers 441 and 442, a voltage amplifier 443 and feedback resistors 451 and 452 according to an embodiment of the invention.

In FIG. 5C the detection signal outputted by gas sensing element 20(j,k) is a current detection signal and the reference signal outputted by reference element 22 is a reference current signal.

Voltage source 423 provide a gate bias voltage to the gases of the CMOS transistors of gas sensing element 20(j,k), a reference element 22.

A detection signal is outputted by gas sensing element 20(j,k) and is a current detection signal. The detection signal reflects the gas sensed by the gas sensing element—especially the temperature of the gas reactive element of gas sensing element 20(j,k). A reference signal is a current detection signal and reflects the temperature of the CMOS transistor of reference element 22.

First transimpedance amplifier 441 receives at its non-inverting input a bias voltage from voltage source 461.

A first current that is a difference between a first fixed current (from first current source 421) and the current detection signal is fed to an inverting input of first transimpedance amplifier 441 and to first feedback resistor 451 to provide a first intermediate voltage that is then fed to a non-inverting input of voltage amplifier 443.

A second current that is a difference between a second fixed current (from second current source 422) and the reference current signal is fed to an inverting input of second transimpedance amplifier 442 and to second feedback resistor 452 to provide a second intermediate voltage that is then fed to an inverting input of voltage amplifier 443.

Voltage amplifier 443 outputs an output signal that represents the difference between the reference signal and the detection signal—which indicates the temperature of the gas reactive element of gas sensing element 20(j,k).

Figure 6:
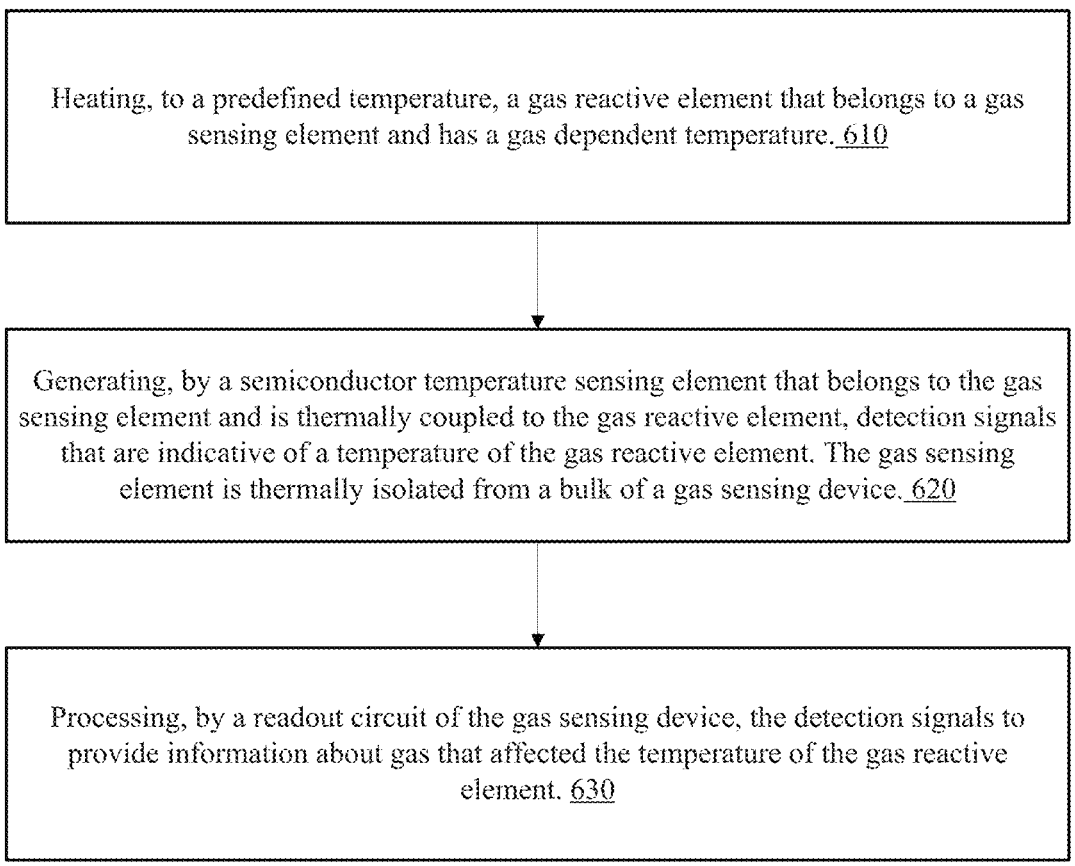
FIG. 6 illustrates a method according to an embodiment of the invention.

FIG. 6 illustrates method 600 according to an embodiment of the invention.

Method 600 may include step 610 of heating, to a predefined temperature, a gas reactive element that belongs to a gas sensing element and has a gas dependent temperature.

Step 610 may be followed by step 620 of generating, by a semiconductor temperature sensing element that belongs to the gas sensing element and is thermally coupled to the gas reactive element, detection signals that are indicative of a temperature of the gas reactive element. The gas sensing element is thermally isolated from a bulk of a gas sensing device.

Step 620 may be followed by step 630 of processing, by a readout circuit of the gas sensing device, the detection signals to provide information about gas that affected the temperature of the gas reactive element.

Method 600 may be executed by any of the gas sensing devices illustrated in any of the drawings.

According to an embodiment of the invention the gas sensing element is distributed—the gas reactive element (that has a gas dependent temperature parameter) is spaced apart from the semiconductor temperature sensing element.

The semiconductor temperature sensing element may sense the radiation (such as blackbody radiation) emitted by the gas reactive element—and is configured to generate detection signals that are responsive to a temperature of the gas reactive element.

The gas reactive element has to interface with the gas but the semiconductor temperature sensing element may be maintained in vacuum—which may greatly increase the sensitivity of the semiconductor temperature sensing element and make the gas sensing more accurate.

The gas reactive element may be shaped as a plate or have any other shape.

The gas reactive element may be heated to a predefined initial temperature by heaters—that are connected to the gas reactive element (and maybe not to the semiconductor temperature sensing element).

The gas reactive element may be shaped as a gas reactive element and may have catalytic material properties. It can be made, for example, from Platinum.

The Platinum can emanate from or be embedded in a thin membrane so that its thermal conductivity is low. The Platinum (or other material) can also be assumed to be porous material emanating from a porous thin membrane (such as silicon dioxide assumed to be porous or porosity).

The gas reactive element has electrical resistance and can be heated to the desired temperature by a supply of an electrical signal via heaters.

The heating can be done in DC and then the temperature of the gas reactive element is determined by the above-invested power and thermal conductivity, The heating can be done in pulses, where the temperature of the gas reactive element is determined by heat capacity and pulse duration Alternatively, the gas reactive element can be embedded in a resistor that is submerged on a membrane and then the resistor may heat the gas reactive element.

The reaction heat increases the temperature of the gas reactive element.

The gas reactive element emits radiation (for example emits radiation like a non-ideal black body)—for example but not limited to infrared radiation.

It has been found that the semiconductor temperature sensing element can operate in sub-conduction.

The self-heating of the semiconductor temperature sensing element is much smaller due to the physical separation.

Each one of the semiconductor temperature sensing element and the gas reactive element can be optimized separately—and independent of the other component.

The gas reactive element can be heated in a non-continuous manner (by pulses) and the semiconductor temperature sensing can be also sampled in a non-continuous manner (for example by using a lock in amplifier)—thus significantly improve the signal to noise ratio of the measurements.

Figure 7:
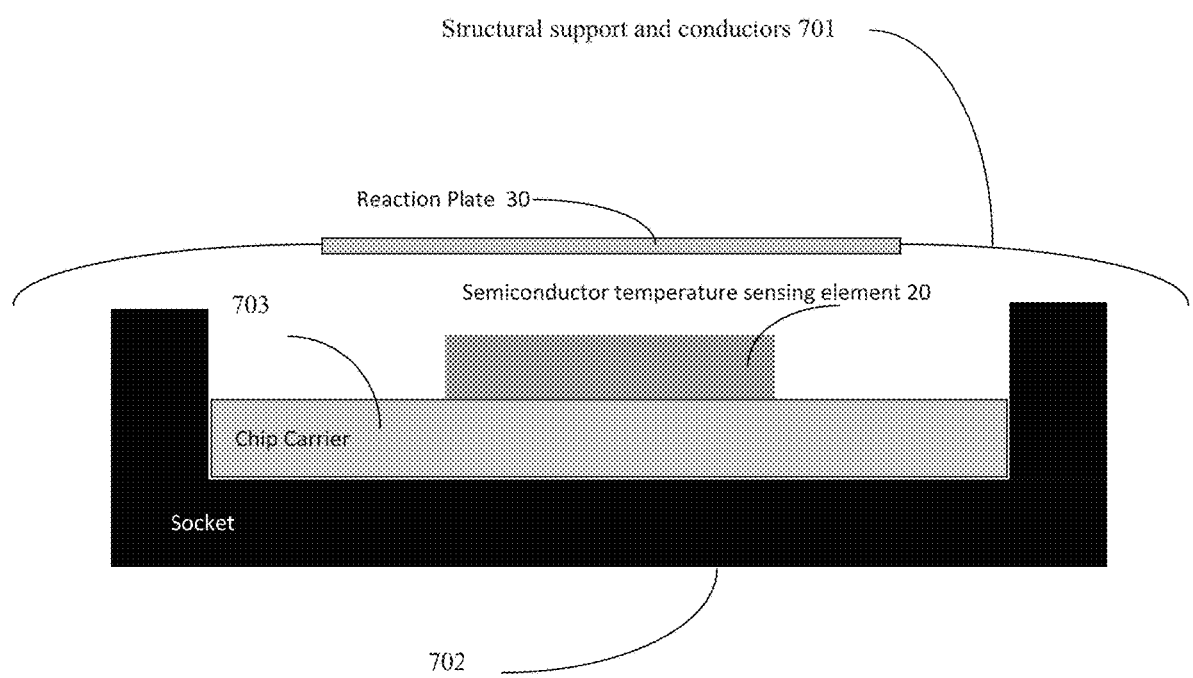
FIG. 7 is a cross sectional view of a setup that includes a gas sensing element according to an embodiment of the invention.
Figure 8:
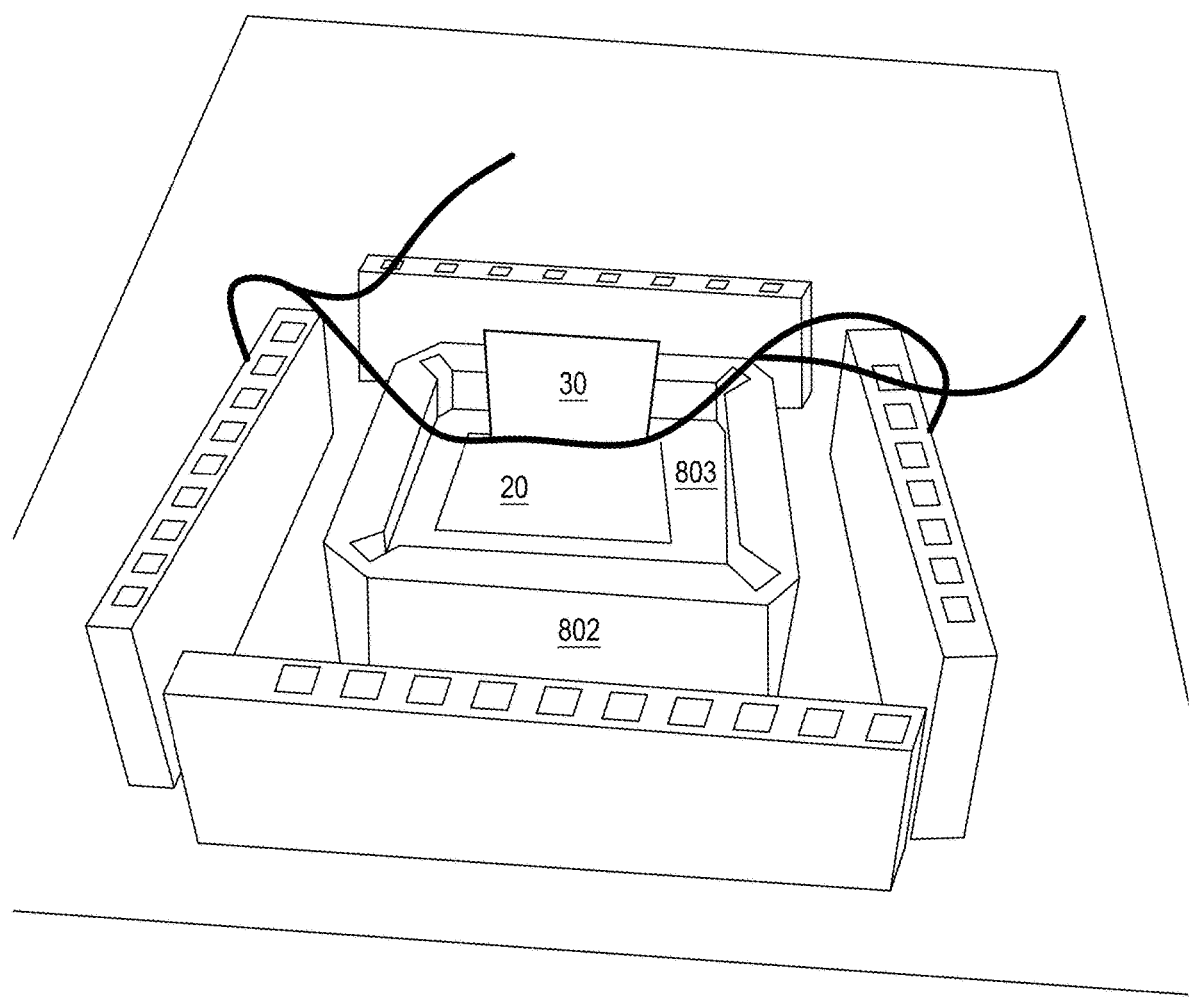
FIG. 8 illustrates a setup that includes a gas sensing element according to an embodiment of the invention.

FIG. 7 is a cross sectional view of a setup that includes a gas sensing element according to an embodiment of the invention. FIG. 8 illustrates a setup that includes a gas sensing element according to an embodiment of the invention.

FIGS. 7 and 8 illustrate a separation between the gas reactive element and the semiconductor temperature sensing element according to an embodiment of the invention. This is merely an example and various other spatial relationships may be provided between the gas reactive element and the semiconductor temperature sensing element.

FIG. 7 illustrates a socket 702 that surrounds a chip carrier 703. The chip carrier may support a chip 20 that may include one or more semiconductor temperature sensing element, one or more readout circuits, one or more interfacing circuits, one or more signals source, and the like. The chip 20 may include one or more semiconductor temperature sensing elements while the one or more readout circuits, one or more interfacing circuits, one or more signals source may be positioned at another chip.

The gas reaction element is a reaction plate 30 that is spaced apart from chip 20. Radiation emitted from the reaction plate 30 is sensed by the semiconductor temperature sensing element of chip 20. The gas reaction element may be a catalytic reaction electrode.

The reaction plate 30 is connected to structural support and conductors 701. The conductors may supply power to a heating element (not shown) for heating the reaction plate 30.

The structural support and conductors 701 may be a part of an enclosure that is sealed and may be configured to maintain vacuum around the chip 20.

In FIG. 8 the setup includes a gas sensing element that include gas reactive element such as reaction plate 30 that has a gas dependent temperature parameter and a spaced apart semiconductor temperature sensing element such as TMOS 3-stack wafer package 20 (or a single die) that is space apart from the gas reactive element 30. The gas reactive element is connected to structural support (not shown) that may also include or support conductors for conveying electrical signals for heating the gas reactive element.

Figure 13:
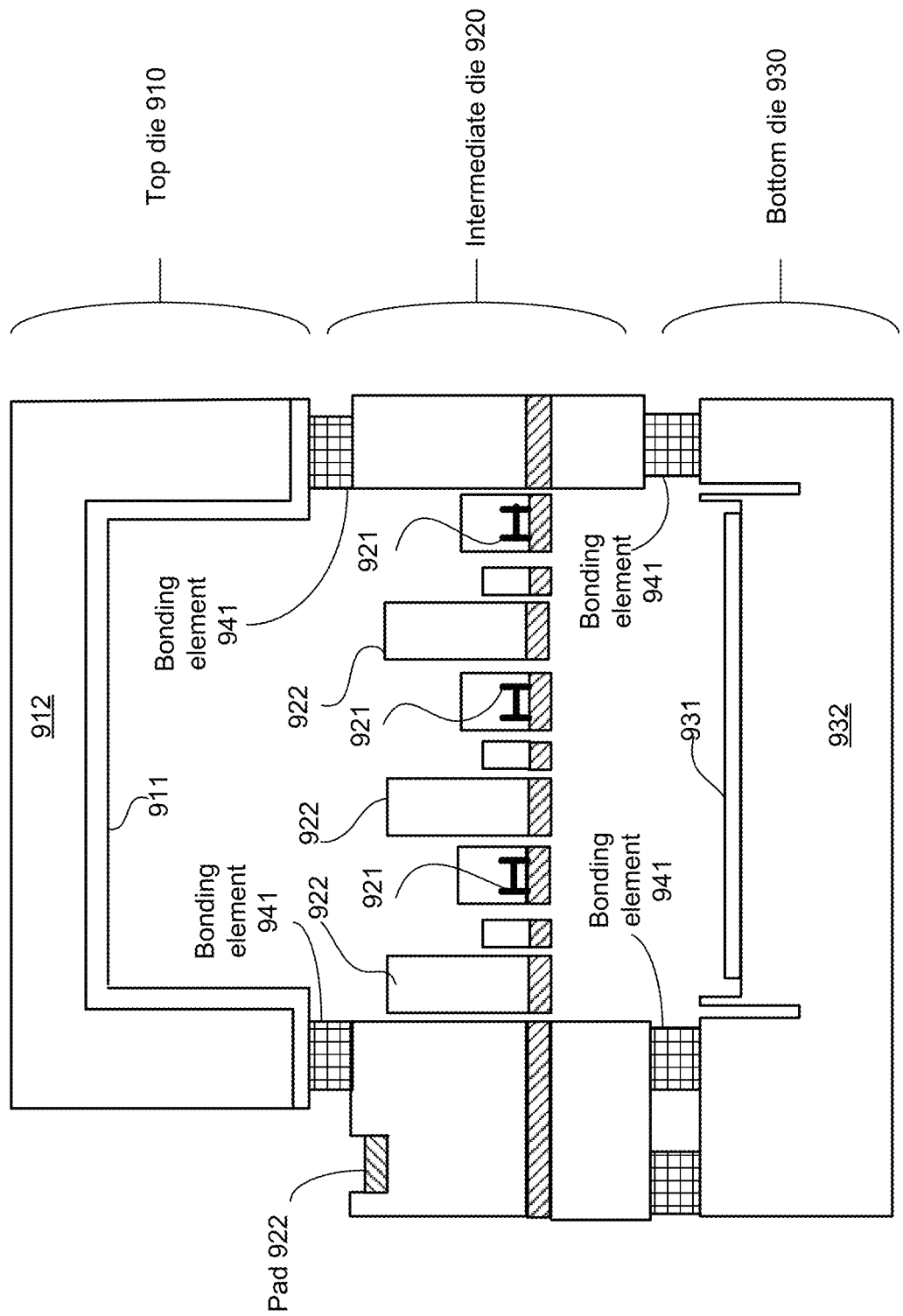
FIG. 13 illustrates a stack of three dies according to an embodiment of the invention.

A non-limiting example of a TMOS-3 stack is shown in FIG. 13. The TMOS-3 stack includes an upper die, a bottom die and an intermediate die. The intermediate die includes the semiconductor temperature sensing element, the upper wafer may include the reaction plate or may not include the reaction plate. The upper and lower dies form a sealed enclosure that enables to place the intermediate die in vacuum.

The vacuum may enable the semiconductor temperature sensing element to sense very low concentration of gas (for example at the order of about 1 part per billion).

Figure 9:
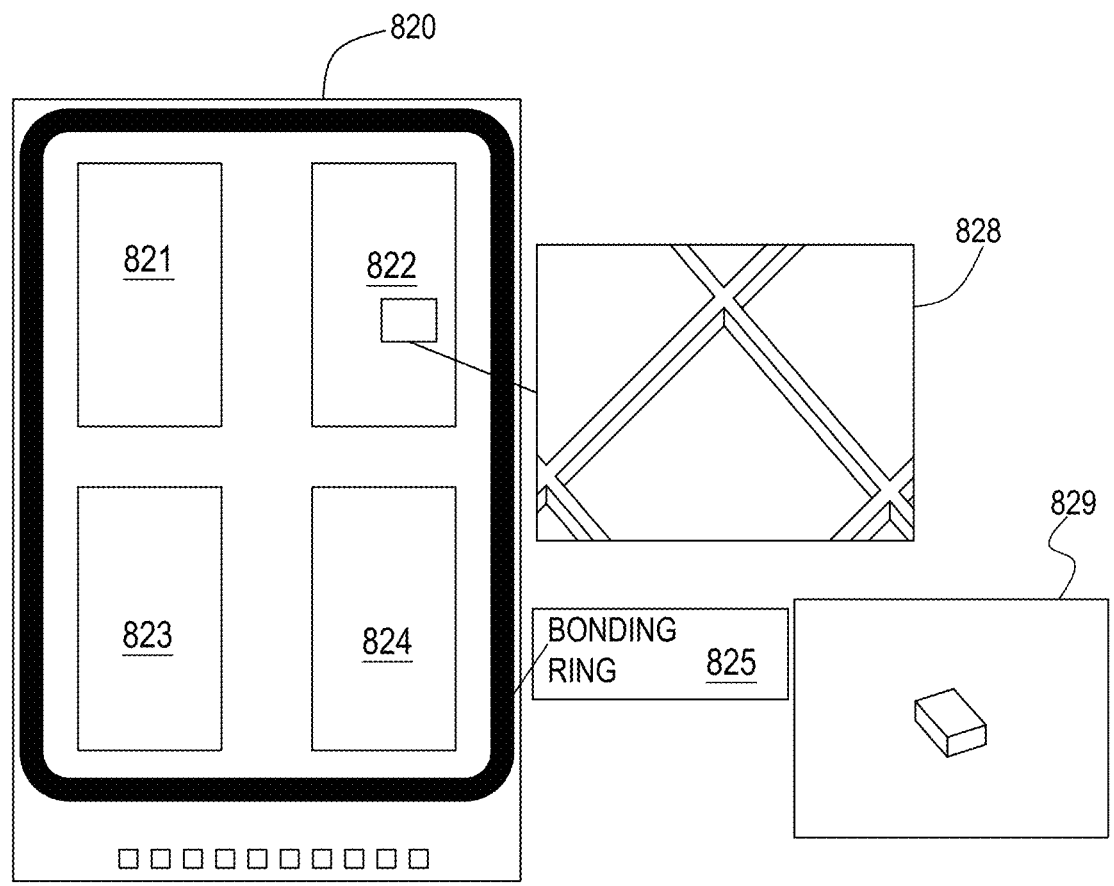
FIG. 9 illustrates multiple pixels according to an embodiment of the invention.

According to an embodiment of the invention the semiconductor temperature sensing element may include one or more pixels—each pixel may include an array of subpixels—as illustrated in FIG. 9 in which there are four pixels 821, 822, 823 and 824 as well as a bounding ring 825. Image 828 is an image of few sub-pixels. Image 829 illustrates the temperature sensing element that is packaged.

The gas reactive element may be electrically conductive and thermally conductive. The gas reactive element should be heated by heating element that is also electrically and thermally conductive. In order to prevent an electrical short between the gas reactive element and the heating element a thermal conductive and electrically isolating interfacing element may be positioned between the gas reactive element and the heating element.

It may also beneficial to increase the area of contact between the gas reactive element and the interfacing element. This can be achieved by using a porous interfacing element and depositing the gas reactive element on the interfacing element or by any other means for creating a non-smooth contact between the interfacing element and the gas reactive element.

Figure 10:
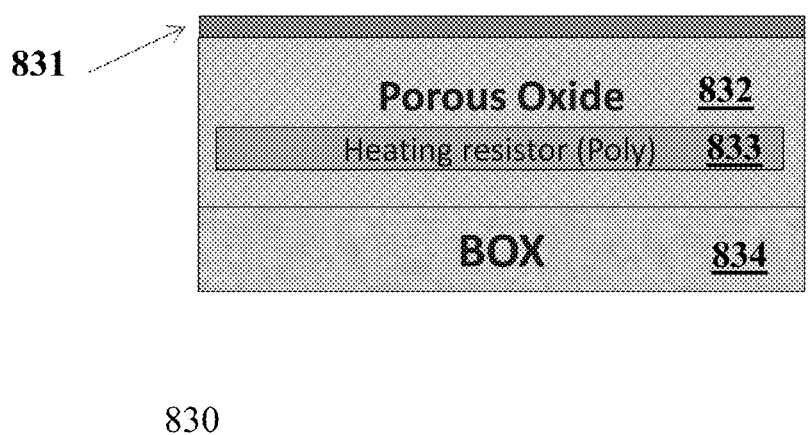
FIG. 10 is a cross sectional view of a semiconductor temperature sensing element according to an embodiment of the invention.

FIG. 10 is a cross section according to an embodiment of the invention in which gas reactive element 831 is deposited on (or otherwise contacts) an interfacing element such as a porous oxide element 832 that surrounds a heating element such as heating resistor 833. The heating resistor can be made of polysilicon or may be made of any other material that is thermal conductive and electrically isolating.

The porous oxide element 832 is deposited on a supporting structure such as a BOX layer 834.

Figure 11:
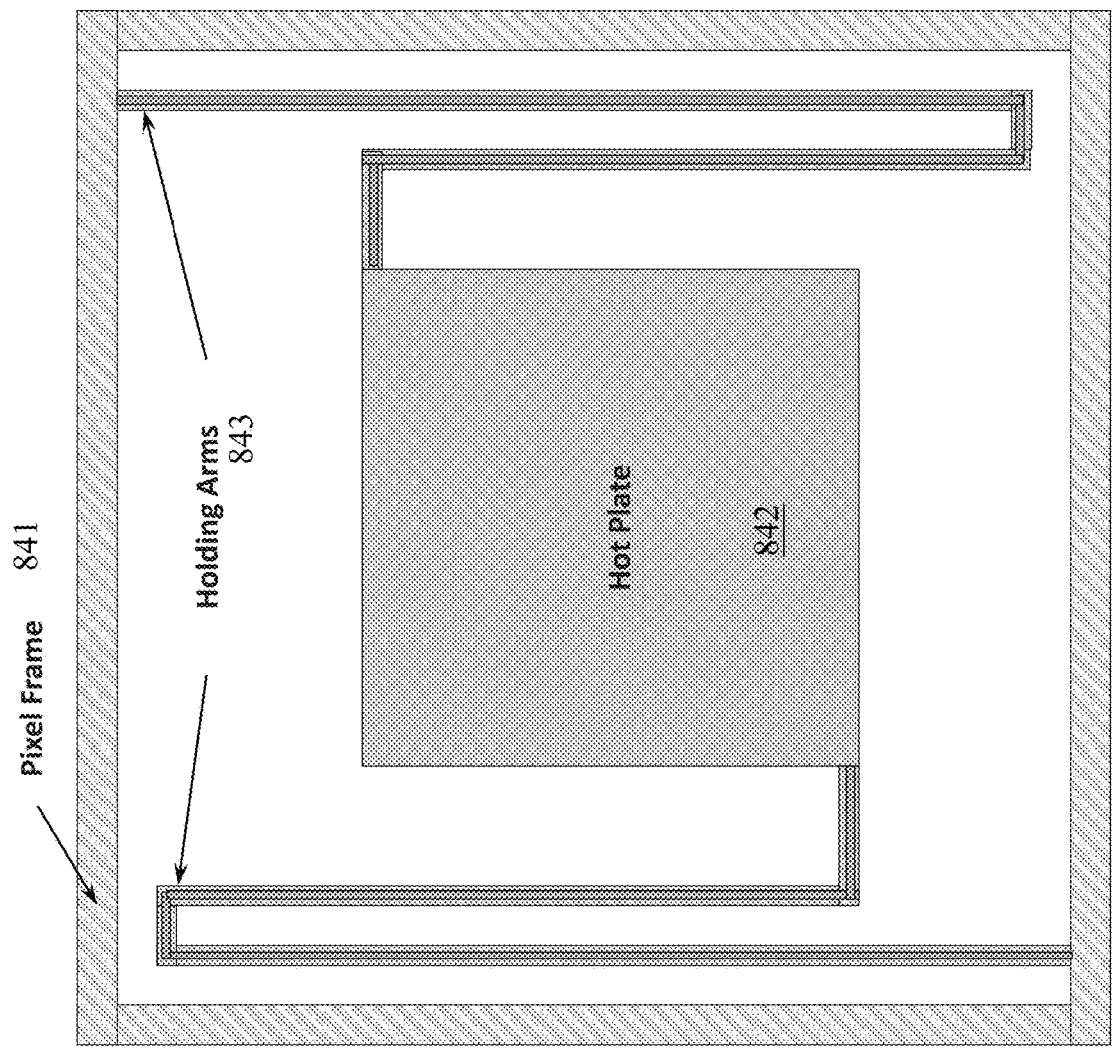
FIG. 11 illustrates a top view of the gas reactive element according to an embodiment of the invention.

FIG. 11 illustrates a top view of the gas reactive element according to an embodiment of the invention. The gas reactive element is shaped as a plate (referred to as hot plate 842) that is supported by holding arms 843 that support conductors for supplying power to a heating element (not shown) positioned below the hot plate 843. The holding arms and the hot plate are suspended (do not contact a bulk). The holding arms 843 are connected to and supported by a pixel frame 841.

It can be seen that the gas reactive element is suspended—and attached by multiple arms to its surroundings.

Figure 12:
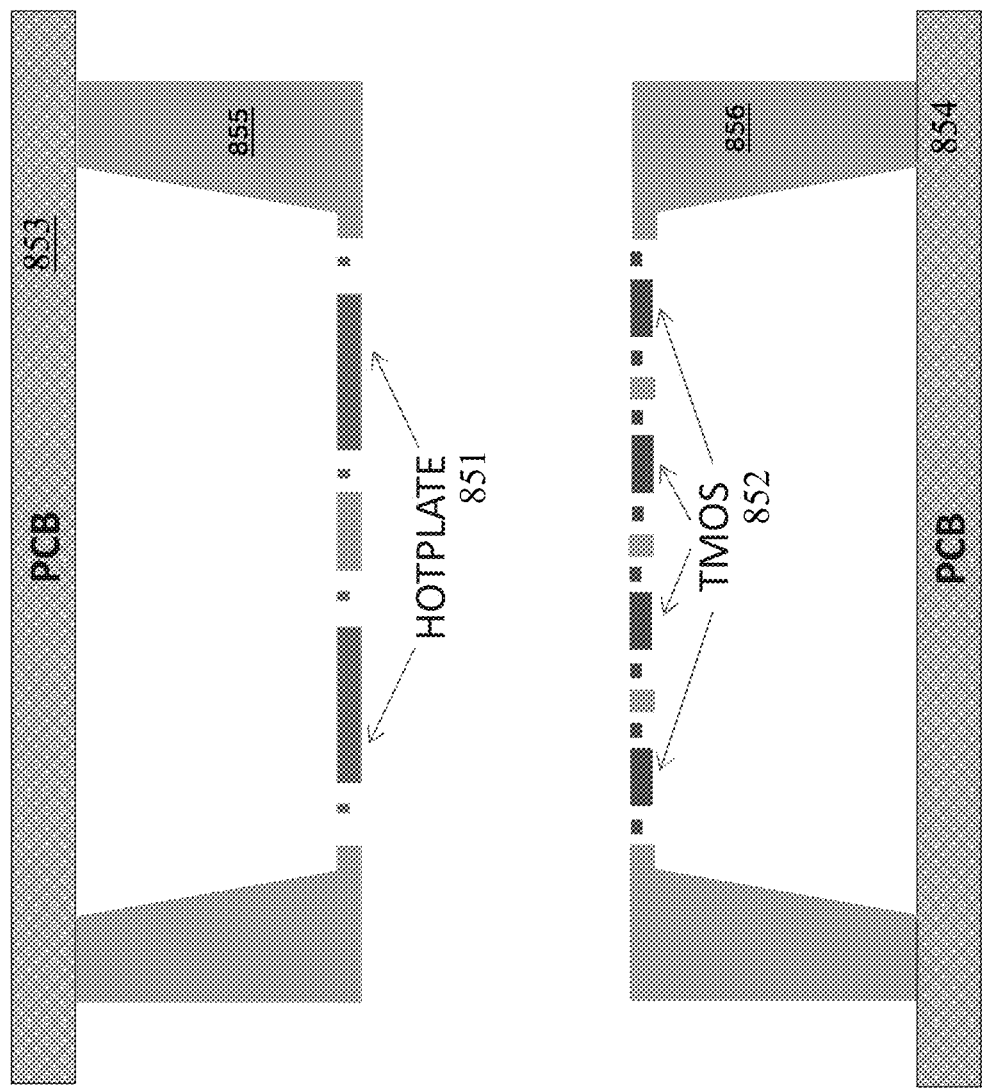
FIG. 12 illustrates a cross sectional view of a gas sensing element that includes a gas reactive element that is separated from and faces semiconductor temperature sensing element according to an embodiment of the invention.

FIG. 12 illustrates a cross sectional view of a gas sensing element that includes a gas reactive element (hotplate) 851 that is supported by support elements 855 that are connected to upper printed circuit board (PCB) 853.

The gas sensing element also includes a semiconductor temperature sensing element (such as a TMOS) 852 that is supported by support elements 856 that are connected to lower PCB 854.

The gas reactive element and the semiconductor temperature sensing element are separated from and face each other.

The gas reactive element and the semiconductor temperature sensing element are suspended above (or below) the upper PCB and the lower PCB respectively.

FIG. 13 is a cross sectional view of a die that includes a top die 810, an intermediate die 820 and a bottom die 830 according to an embodiment of the invention.

The intermediate die 820 includes one or more semiconductor temperature sensing elements 921 and parts of frames and/or arms 922. The intermediate die 920 includes multiple apertures and in order to provide a closed chamber the intermediate die 920 has to be surrounded (both on top and on bottom) by top die 910 and bottom die 930.

In FIG. 13 the bottom die 930 serves as an optical window with a filter (lambda half cavity-remove) and includes a bulk 932 and reflecting element 931.

In FIG. 13 the top die 910 includes bulk 912 and oxide 911 for preventing a formation of a ghost image. The gas reactive element may be attached to the bulk 912, integrated with the bulk or may be spaced apart from the bulk 912.

FIG. 13 illustrated bonding elements such as 941 between the dies and also shows pads 933 for supplying input signals and receiving output signals.

Various readout setups may be provided and may include voltage sensing and current sensing. Each one of the voltage and current sensing may include differential sensing (using a reference sensing element) or single-ended sensing (no reference sensing element). Each one of the voltage and current sensing may include supplying a DC (direct current) bias signals, pulsed bias signals and modulated bias signals or a combination thereof. A non-limiting example of a modulated bias signal and/or a modulated heating signal may include a signal that is a superposition of a DC pulse (a jump from a first DC level to a second DC level that is followed, after a certain period, by a jump from the second DC level to the first DC level) and a sinusoidal signal or any other signal that may change multiple times during the certain period.

FIGS. 14-19 illustrate various options for readout circuits according to various embodiments of the invention.

FIGS. 14-19 illustrate biasing signals that bias reference sensing element 864 and gas sensing element 865. Different signals (that may be synchronized with the bias signals) are provided to the gas sensing elements for heating the gas sensing elements associated with the reference sensing element 864 and gas sensing element 865.

According to various embodiments of the invention the readout of the semiconductor temperature sensing element can be based either on voltage or current, in a bridge like configuration where the readout circuit measures the difference between Active Reaction Plate (with catalytic electrode) and Reference Reaction electrode (with just the resistor).

According to an embodiment of the invention each one of the gas reactive element and the semiconductor temperature sensing element can be packaged on its PCB and the gas reactive element and the semiconductor temperature sensing element may be positioned in close proximity (for example—in micron or nanometric scale) so that each semiconductor temperature sensing element may detects the thermal radiation of the corresponding gas reactive element According to an embodiment of the invention there may be provided one or more reference semiconductor temperature sensing element. Such a reference semiconductor temperature sensing element may face a heating resistor that is not coupled to a gas reactive element. And it detects only the thermal radiation due to the heating resistor According to an embodiment of the invention the signals (current/voltage) supplied to each one of the gas reactive element and the semiconductor temperature sensing element can be modulated independently.

Each one of FIGS. 14-19 illustrates current sources 861 and 862 that output current pulses. The current pulses are only a non-limiting example of current signals that may be provided by current sources 861 and 861. For example—the current sources 861 and 862 may output a constant current signal.

Figure 14:
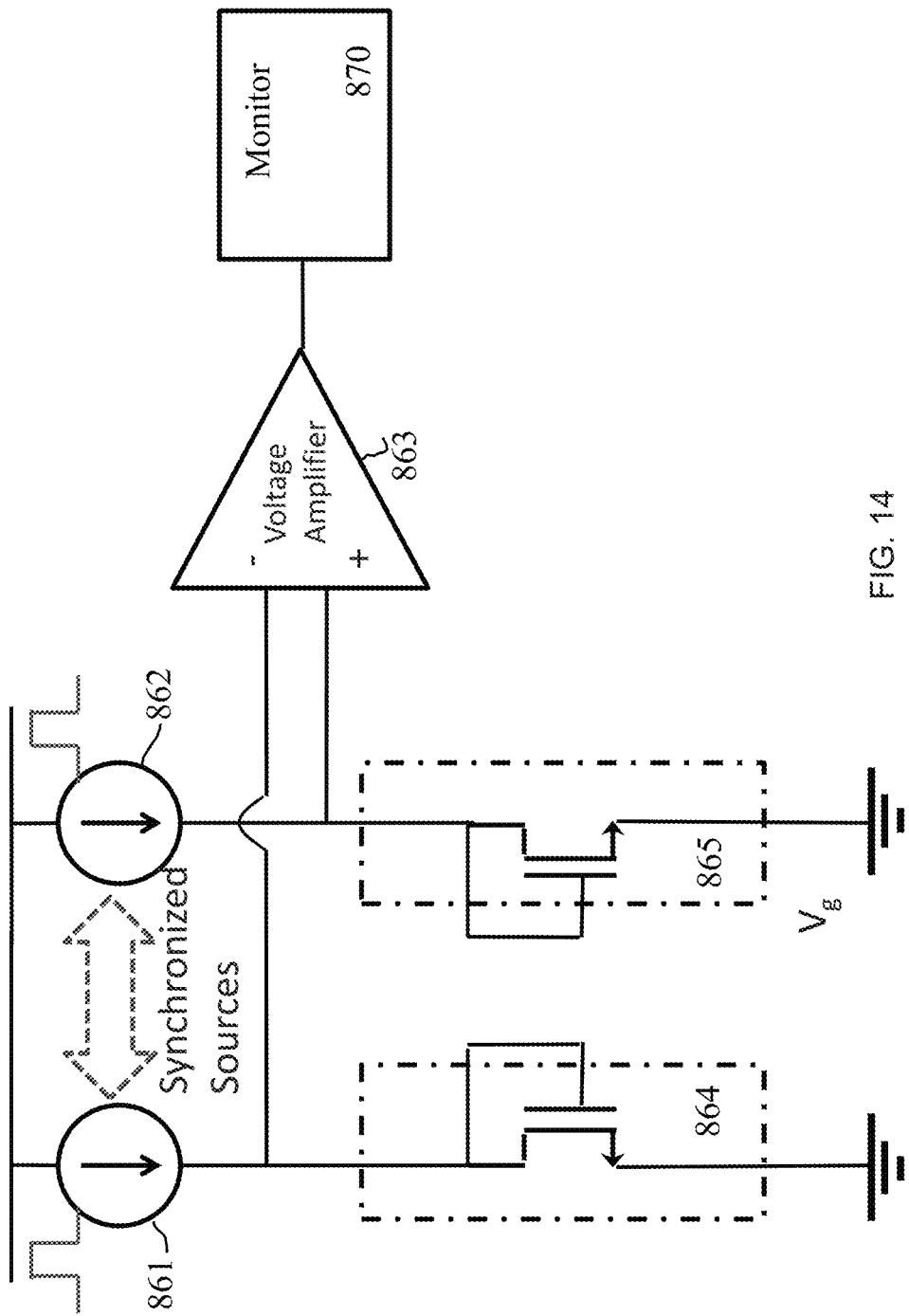
FIGS. 14-19 illustrate various options for readout circuits according to various embodiments of the invention.

FIG. 14 illustrates a circuit 860 for differential voltage mode sensing according to an embodiment of the invention.

Synchronized current sources 861 and 862 that supply (for example—in a synchronized manner) current pulses for biasing reference sensing element 864 and gas sensing element 865.

A differential amplifier (voltage amplifier) 863 measures a voltage difference between the voltage drop across the reference sensing element 864 and gas sensing element 865 and output to monitor 870 an output signal indicative of the voltage difference.

The voltage difference is indicative of the temperature sensed by the gas sensing element of the gas sensing element 865.

The reference heating element (of the reference sensing element 864) and the heating element of the gas sensing element 865 may receive the same heating signals.

Figure 15:
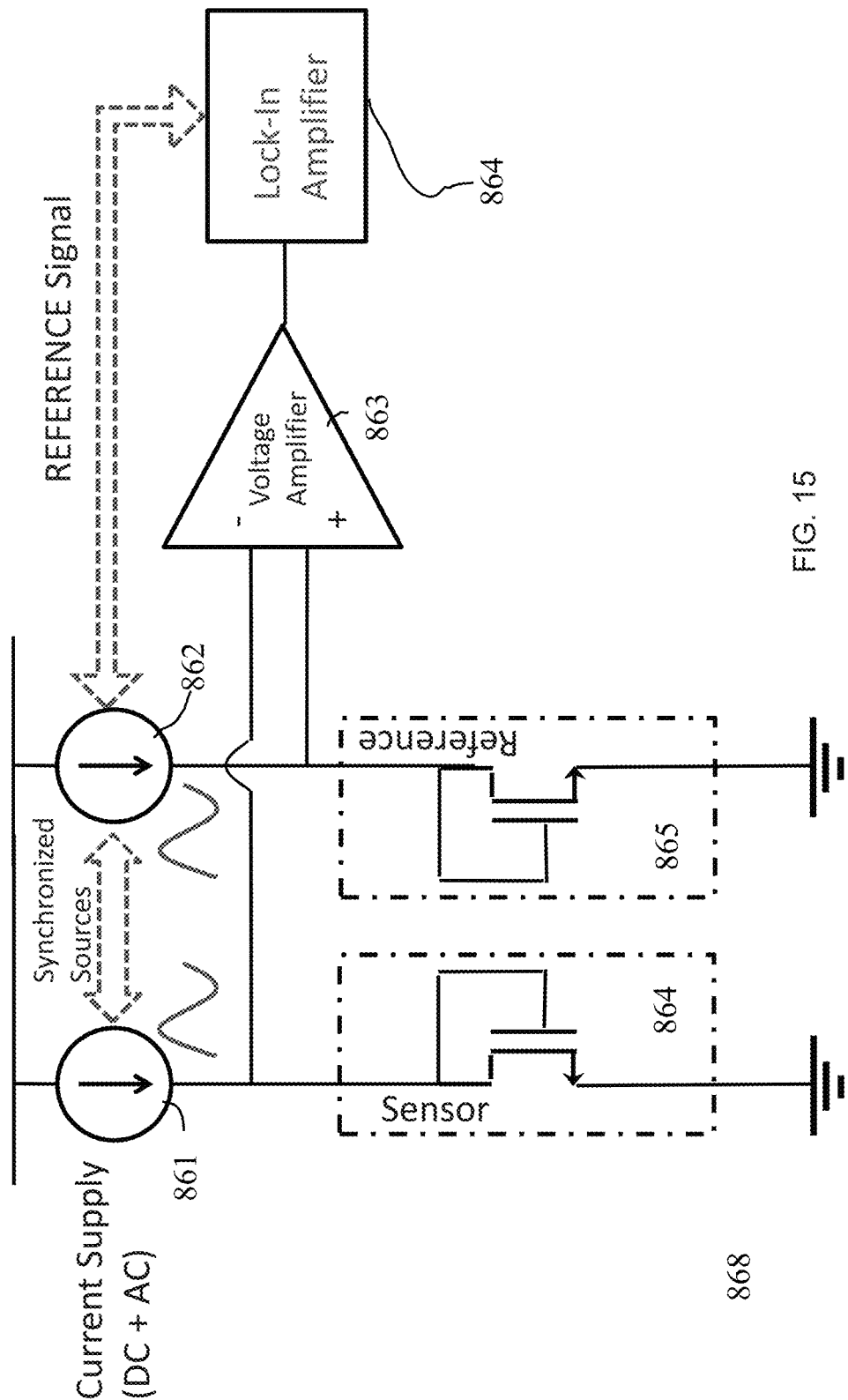

FIG. 15 illustrates a circuit 868 for modulated differential voltage mode sensing using a lock-in amplifier according to an embodiment of the invention.

The lock-in amplifier increases the signal to noise ratio of the measurements.

According to an embodiment of the invention the biasing signals provided by current sources 861 and 862 to the reference sensing element 864 and gas sensing element 865 are modulated (regardless of the bias signals supplied to the semiconductor temperature sensing element). The heating signals provided to the gas sensing elements of the reference sensing element 864 and gas sensing element 865 may also be modulated—even by the same modulation.

The lock-in amplifier follows the differential amplifier (voltage amplifier) 863 and may detect only signals and noise corresponding to the modulating frequency and hence a lot of noise is rejected.

Figure 16:
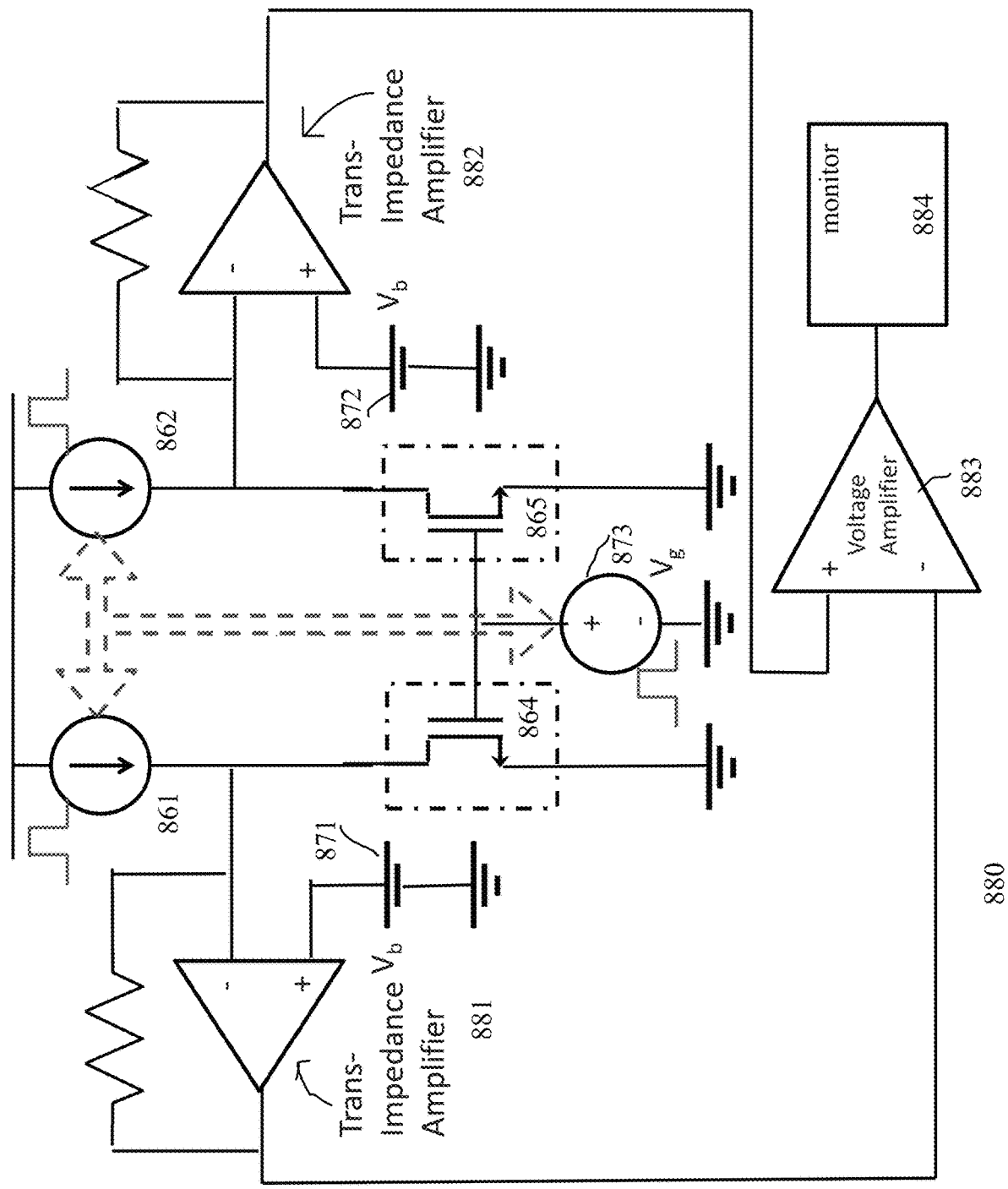

FIG. 16 illustrates a circuit 880 for differential current mode sensing according to an embodiment of the invention.

Synchronized current sources 861 and 862 supply (for example—in a synchronized manner) current pulses for biasing the heating elements of reference sensing element 864 and gas sensing element 865.

The reference sensing element 864 and gas sensing element 865 are also fed with an additional bias voltage by bias voltage supply 873.

Transimpedance amplifiers 881 and 882 sample the currents that flows through the reference sensing element 864 and the gas sensing element 865 and convert the sampled currents to voltage signals that are fed to differential amplifier (voltage amplifier) 863 that measures a voltage difference between the voltage signals outputted by the transimpedance amplifiers 881 and 882 and outputs to monitor 844 an output signal indicative of the voltage difference. The voltage difference is indicative of the temperature sensed by the gas sensing element of the gas sensing element 865.

Transimpedance amplifiers 881 and 882 include differential amplifiers and resistors. The differential amplifiers are fed by a constant bias voltage from bias sources 871 and 872.

Figure 17:
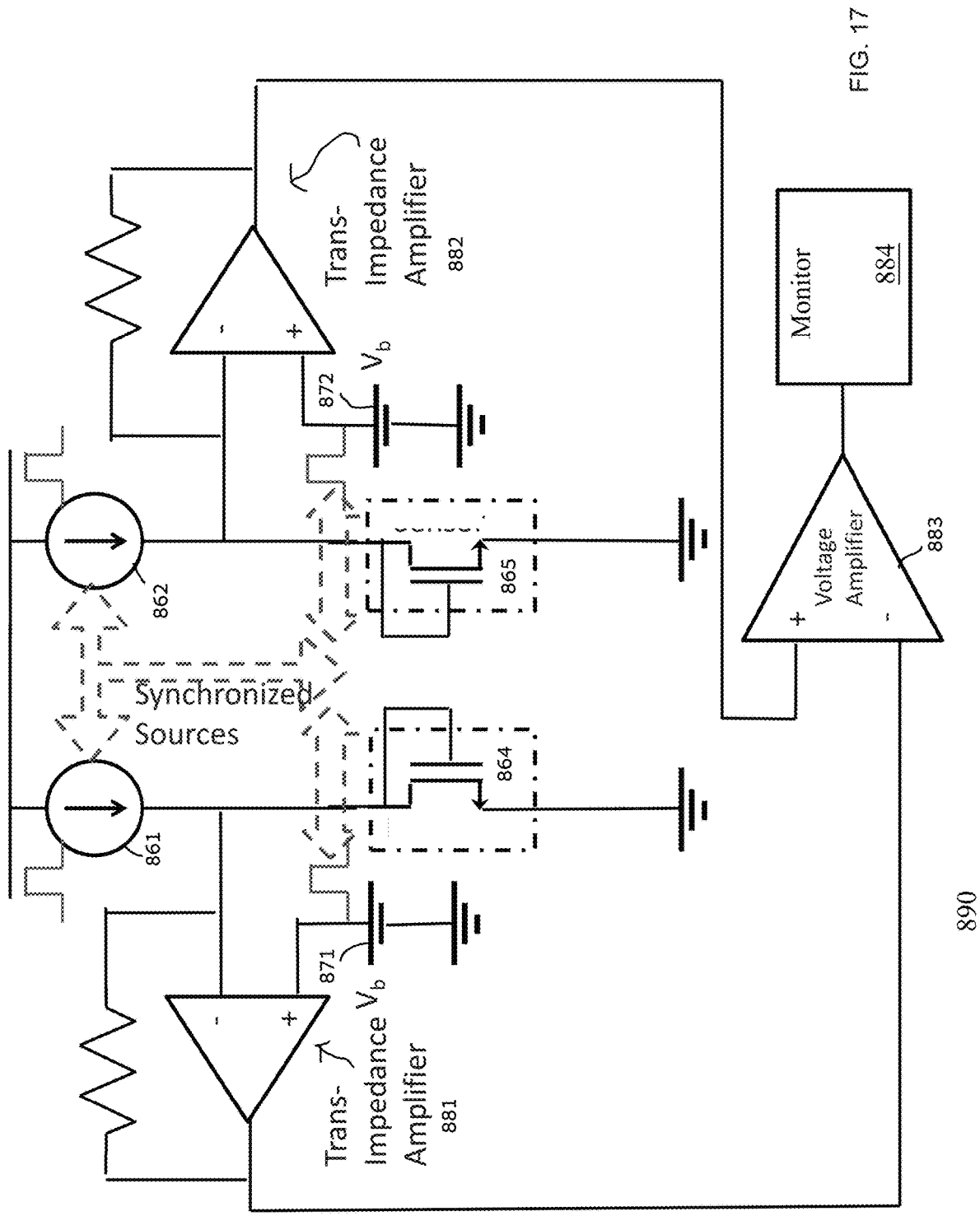

FIG. 17 illustrates a circuit 890 for differential current mode sensing according to an embodiment of the invention.

FIG. 17 differs from FIG. 16 by the supply of bias voltages pulses (instead of a constant bias voltage) from bias sources 871 and 872. The bias voltages pulses may be synchronized with the current pulses supplied by current sources 861 and 862.

A differential amplifier (voltage amplifier) 863 measures a voltage difference between the voltage drop across the reference sensing element 864 and gas sensing element 865 and output to monitor 870 an output signal indicative of the voltage drop. The voltage drop is indicative of the temperature sensed by the gas sensing element of the and gas sensing element 865.

The reference heating element (of the reference sensing element 864) and the heating element of the gas sensing element 865 may receive the same heating signals.

Figure 18:
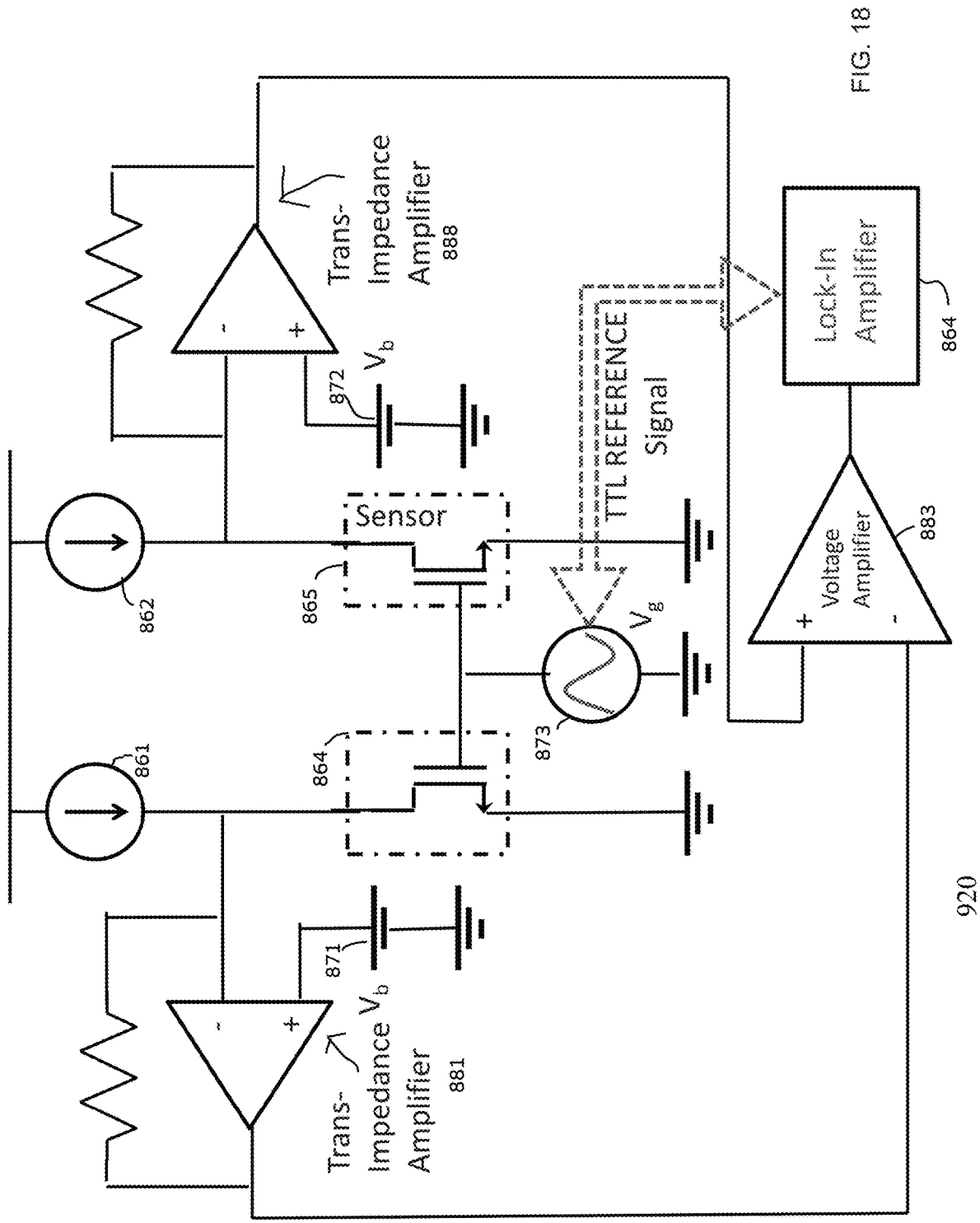

FIG. 18 illustrates a circuit 920 for differential current mode sensing according to an embodiment of the invention.

FIG. 18 differs from FIG. 16 by the supply of modulated voltage from bias voltage supply 873 and by the usage of a lock in amplifier 864 instead of monitor 884.

Figure 19:
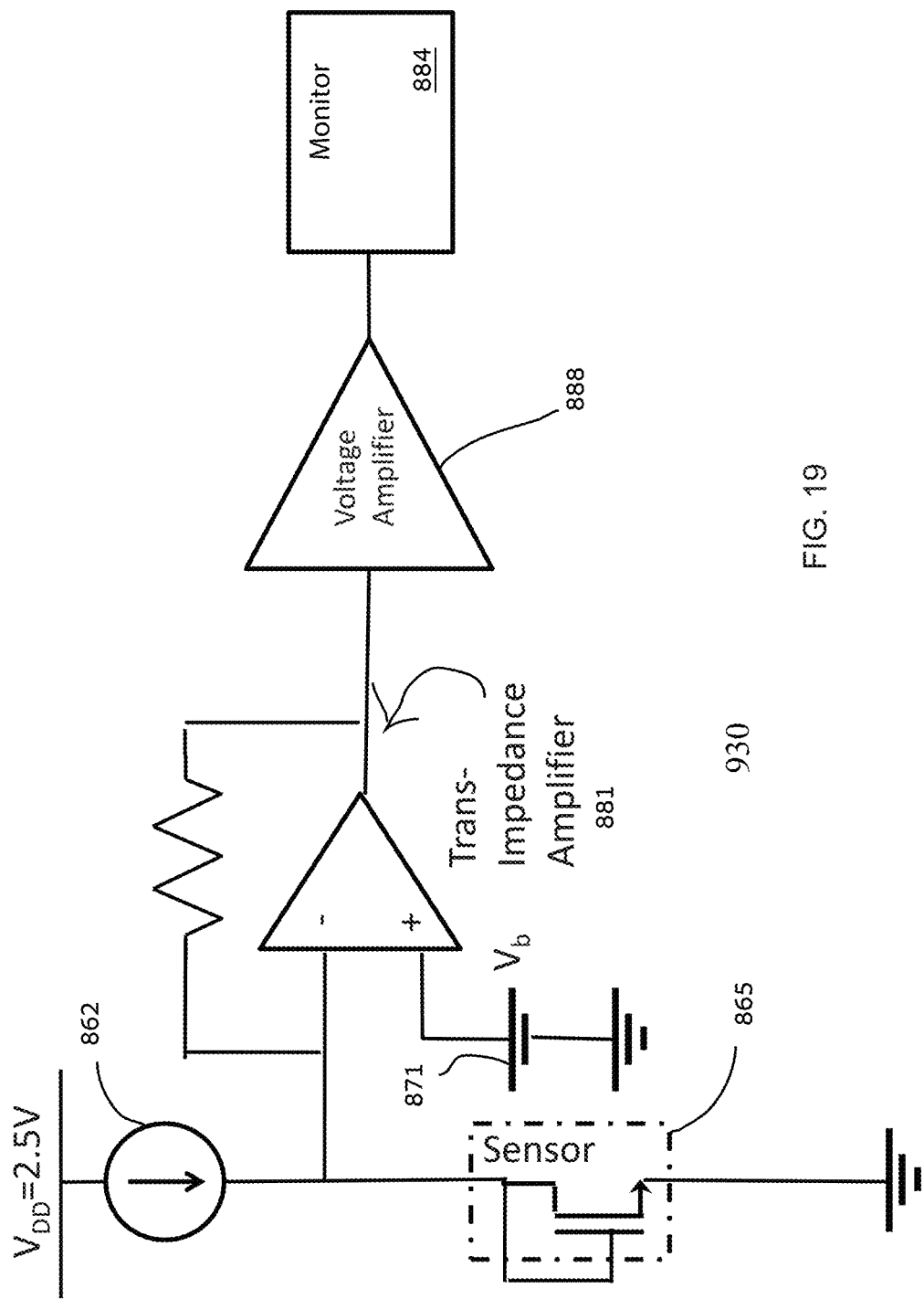

FIG. 19 illustrates a circuit 930 for single terminal current mode sensing according to an embodiment of the invention.

FIG. 19 does not include a reference sensing element.

Current sources 862 supplies current pulses for biasing the gas sensing element 865.

Transimpedance amplifier 882 samples the current that flows through the gas sensing element 865 and converts the sampled current to voltage signals that are fed to voltage amplifier 888. The voltage amplifier 888 outputs to monitor 844 an output signal indicative of the voltage signals. The voltage signals are indicative of the temperature sensed by the gas sensing element of the gas sensing element 865.

According to an embodiment of the invention the gas sensing element can be calibrated by applying a voltage/current corresponding to ZTC (zero temperature coefficient).

FIG. 20 illustrates method 950 according to an embodiment of the invention.

Method 950 may start by step 952 of generating, by a semiconductor temperature sensing element that is spaced apart from a gas reactive element and is thermally coupled to the gas reactive element, detection signals that are indicative of a temperature of the gas reactive element; wherein the gas reactive element and the semiconductor temperature sensing element are of microscopic scale. Microscopic scale may indicate that one or more of the dimensions of the gas reactive element and the semiconductor temperature sensing element are of a micron or sub-micron scale. For example—a width, length and/or thickness of the gas reactive element and the semiconductor temperature sensing element may be below 100 microns, below 10 microns, below a micron, below 100 nanometers, below 10 nanometers and/or below 1 nanometer.

Step 952 may be followed by step 954 of processing, by a readout circuit of the gas sensing device, the detection signals to provide information about a gas that affected the temperature of the gas reactive element.

There may be provided a mapping (equation, lookup table) between the temperature of the gas reactive element and the concentration of gas sensed by the temperature of the gas reactive element. The mapping may be used for determining the concentration of gas based on the detection signals.

The gas sensing element may be configured (at least during a certain period) to sense a specific gas. This can be obtained, for example, by the composition of the gas reactive element and/or by the temperature to which the gas reactive element is heated to.

Accordingly—when set to sense a specific gas the detection signals indicate the concentration of that certain gas.

Method 950 may be executed by any of the gas sensing devices illustrated in the specification.

Method 950 may also include step 951 of heating the heating element, step 953 of maintaining vacuum within an enclosure that surrounds the semiconductor temperature sensing element, step 955 of using differential sensing that involve reading detection signals from a reference semiconductor temperature sensing element that does not sense radiation from a gas reactive element, step 957 of using multiple gas sensing elements (each includes a gas reactive element that is spaced apart from a semiconductor temperature sensing element), and the like.

Step 957 may include setting N gas sensing elements, at a certain point in time, to sense different gases; and detecting a composition of up till N different gaseous materials by processing the detection signals from the N gas sensing elements.

In the foregoing specification, the invention has been described with reference to specific examples of embodiments of the invention. It will, however, be evident that various modifications and changes may be made therein without departing from the broader spirit and scope of the invention as set forth in the appended claims.

Moreover, the terms "front," "back," "top," "bottom," "over," "under" and the like in the description and in the claims, if any, are used for descriptive purposes and not necessarily for describing permanent relative positions. It is understood that the terms so used are interchangeable under appropriate circumstances such that the embodiments of the invention described herein are, for example, capable of operation in other orientations than those illustrated or otherwise described herein.

The connections as discussed herein may be any type of connection suitable to transfer signals from or to the respective nodes, units or devices, for example via intermediate devices. Accordingly, unless implied or stated otherwise, the connections may for example be direct connections or indirect connections. The connections may be illustrated or described in reference to being a single connection, a plurality of connections, unidirectional connections, or bidirectional connections. However, different embodiments may vary the implementation of the connections. For example, separate unidirectional connections may be used rather than bidirectional connections and vice versa. Also, plurality of connections may be replaced with a single connection that transfers multiple signals serially or in a time multiplexed manner. Likewise, single connections carrying multiple signals may be separated out into various different connections carrying subsets of these signals. Therefore, many options exist for transferring signals.

Although specific conductivity types or polarity of potentials have been described in the examples, it will be appreciated that conductivity types and polarities of potentials may be reversed.

Any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermedial components. Likewise, any two components so associated can also be viewed as being "operably connected," or "operably coupled," to each other to achieve the desired functionality.

However, other modifications, variations and alternatives are also possible. The specifications and drawings are, accordingly, to be regarded in an illustrative rather than in a restrictive sense.

In the claims, any reference signs placed between parentheses shall not be construed as limiting the claim. The word 'comprising' does not exclude the presence of other elements or steps then those listed in a claim. Furthermore, the terms "a" or "an," as used herein, are defined as one or more than one. Also, the use of introductory phrases such as "at least one" and "one or more" in the claims should not be construed to imply that the introduction of another claim element by the indefinite articles "a" or "an" limits any particular claim containing such introduced claim element to inventions containing only one such element, even when the same claim includes the introductory phrases "one or more" or "at least one" and indefinite articles such as "a" or "an." The same holds true for the use of definite articles. Unless stated otherwise, terms such as "first" and "second" are used to arbitrarily distinguish between the elements such terms describe. Thus, these terms are not necessarily intended to indicate temporal or other prioritization of such elements.

The mere fact that certain measures are recited in mutually different claims does not indicate that a combination of these measures cannot be used to advantage.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

We claim:

1. A method for sensing gas by a gas sensing device, the method comprises:
   heating a gas reactive element, by a heating element that is thermally coupled to the gas reactive element, and at different points in time, to different predefined temperatures of multiple predefined temperatures, the multiple predefined temperatures are associated with a sensing of multiple gases that differ from each other;
   generating detection signals, at the different points in time and by a semiconductor temperature sensing element that is spaced apart from the gas reactive element and is thermally coupled to the gas reactive element; wherein the gas reactive element and the semiconductor temperature sensing element are of microscopic scale; and
   processing, by a readout circuit of the gas sensing device, the detection signals to provide information about one or more gases that affected the temperatures of the gas reactive element; wherein the one or more gases belong to the multiple gases that differ from each other.

2. The method according to claim comprising supplying to a heating element that is thermally coupled to the gas reactive element, a predefined amount of heat to the gas reactive element.

3. The method according to claim 2, wherein the heating element and the gas reactive element are thermally coupled to each other through a thermally conductive and electrically isolating element.

4. The method according to claim 1, comprising heating the gas reactive element to a predefined temperature, by a heating element that is thermally coupled to the gas reactive element.

5. The method according to claim 1, wherein the semiconductor temperature sensing element is located within an enclosure and the gas reactive element is not located within the enclosure.

6. The method according to claim 5, comprising maintaining vacuum within the enclosure.

7. The method according to claim 5, wherein the gas reactive element is connected to the enclosure.

8. The method according to claim 5, wherein the gas reactive element is not connected to the enclosure.

9. The method according to claim 1, further comprising detecting, by a reference semiconductor temperature sensing element, heat generated by a reference heating element;
wherein the reference semiconductor temperature sensing element is not thermally coupled to a gas reactive element.

10. The method according to claim 1, comprising:
heating gas reactive elements, by heating elements that are thermally coupled to the gas reactive elements, and at the different points in time, to the different predefined temperatures;
generating detection signals, at the different points in time and by semiconductor temperature sensing elements that are spaced apart from the gas reactive elements and are thermally coupled to the gas reactive elements; wherein the gas reactive elements and the semiconductor temperature sensing elements are of microscopic scale; and
processing, by the readout circuit, the detection signals to provide information about one or more gases that affected the temperatures of the gas reactive elements; wherein the one or more gases belong to the multiple gases that differ from each other.

11. The method according to claim 10, wherein the semiconductor temperature sensing elements are thermally isolated from each other.

12. The method according to claim 10, comprising generating reference detection signals by at least one reference semiconductor temperature sensing element that is not thermally coupled to any of the gas reactive elements.

13. The method according to claim 10, wherein the gas sensing elements comprise N gas sensing elements; wherein the method comprises setting the N gas sensing elements, at a certain point in time, to sense different gases; and detecting a composition of up till N different gaseous materials by processing the detection signals from the N gas sensing elements.

14. The method according to claim 1, wherein the heating element is a polysilicon resistor.

15. The method according to claim 1 comprising heating, by each heating element, a gas reactive element in a non-continuous manner.

\* \* \* \* \*